(12) United States Patent
Wostyn

(10) Patent No.: US 10,874,798 B2
(45) Date of Patent: Dec. 29, 2020

(54) THERAPEUTIC APPLICATIONS OF ARTIFICIAL CEREBROSPINAL FLUID AND TOOLS PROVIDED THEREFOR

(71) Applicant: P&X MEDICAL NV, Oostkamp (BE)

(72) Inventor: Peter Wostyn, Oostduinkerke (BE)

(73) Assignee: P&X Medical NV, Oostkamp (BE)

( * ) Notice: Subject to any disclaimer, the term of this patent is extended or adjusted under 35 U.S.C. 154(b) by 224 days.

(21) Appl. No.: 15/517,983

(22) PCT Filed: Oct. 15, 2015

(86) PCT No.: PCT/EP2015/073893
§ 371 (c)(1),
(2) Date: Apr. 10, 2017

(87) PCT Pub. No.: WO2016/059162
PCT Pub. Date: Apr. 21, 2016

(65) Prior Publication Data
US 2018/0228970 A1  Aug. 16, 2018

Related U.S. Application Data

(60) Provisional application No. 62/064,321, filed on Oct. 15, 2014.

(30) Foreign Application Priority Data

Apr. 17, 2015  (EP) .................................. 15163949

(51) Int. Cl.
*A61M 5/172* (2006.01)
*A61K 38/19* (2006.01)
(Continued)

(52) U.S. Cl.
CPC ......... *A61M 5/1723* (2013.01); *A61K 9/0019* (2013.01); *A61K 9/0085* (2013.01);
(Continued)

(58) Field of Classification Search
CPC .... A61K 35/30; A61K 38/193; A61K 9/0019; A61K 9/0085; A61M 2202/0464;
(Continued)

(56) References Cited

U.S. PATENT DOCUMENTS 5,641,749 A * 6/1997 Yan ..................... A61K 38/185
514/8.4
6,264,625 B1  7/2001 Rubenstein et al.
(Continued)

FOREIGN PATENT DOCUMENTS

CN         2897269 Y     5/2007
CN       101548986 A    10/2009
(Continued)

OTHER PUBLICATIONS

PCT International Search Report and Written Opinion dated Mar. 23, 2016 for PCT International Patent Application No. PCT/EP2015/073893, 20 pages.
(Continued)

*Primary Examiner* — Lauren P Farrar
(74) *Attorney, Agent, or Firm* — Amster, Rothstein & Ebenstein LLP

(57) ABSTRACT

Described herein is the use of CSF, more particularly external CSF or CSF-like compositions for the treatment and prevention of different diseases. More particularly, the application provides for the administration of CSF to the intrathecal space or the cerebral ventricles of a patient to increase intracranial pressure and/or CSF flow.

17 Claims, 7 Drawing Sheets

(51) Int. Cl.

| | |
|---|---|
| *A61K 35/30* | (2015.01) |
| *A61K 9/00* | (2006.01) |
| *A61M 27/00* | (2006.01) |
| *A61M 5/142* | (2006.01) |
| *A61P 27/06* | (2006.01) |
| *G16H 40/67* | (2018.01) |
| *G16H 20/17* | (2018.01) |
| *G16H 50/20* | (2018.01) |
| *G16H 40/63* | (2018.01) |

(52) U.S. Cl.
CPC ............ *A61K 35/30* (2013.01); *A61K 38/193* (2013.01); *A61M 5/14276* (2013.01); *A61M 27/006* (2013.01); *A61P 27/06* (2018.01); *A61M 2202/0464* (2013.01); *A61M 2230/005* (2013.01); *G16H 20/17* (2018.01); *G16H 40/63* (2018.01); *G16H 40/67* (2018.01); *G16H 50/20* (2018.01)

(58) Field of Classification Search
CPC .......... A61M 2230/005; A61M 27/006; A61M 5/14276; A61M 5/1723; A61P 27/06; G16H 20/17; G16H 40/67
See application file for complete search history.

(56) References Cited

U.S. PATENT DOCUMENTS

| | | | |
|---|---|---|---|
| 9,168,172 B1* | 10/2015 | Berdahl | ............... A61F 9/00781 |
| 9,901,650 B2 | 2/2018 | Nedergaard et al. | |
| 2004/0220518 A1 | 11/2004 | Heruth et al. | |
| 2004/0220543 A1 | 11/2004 | Heruth et al. | |
| 2004/0220544 A1 | 11/2004 | Heruth et al. | |
| 2004/0220545 A1 | 11/2004 | Heruth et al. | |
| 2004/0220546 A1 | 11/2004 | Heruth et al. | |
| 2004/0220547 A1 | 11/2004 | Heruth et al. | |
| 2004/0220548 A1 | 11/2004 | Heruth et al. | |
| 2004/0220552 A1 | 11/2004 | Heruth et al. | |
| 2005/0090549 A1 | 4/2005 | Hildebrand et al. | |
| 2010/0069841 A1 | 3/2010 | Miesel | |
| 2010/0168607 A1 | 7/2010 | Miesel | |
| 2010/0179518 A1 | 7/2010 | Ludvig et al. | |
| 2010/0305492 A1 | 12/2010 | Lad et al. | |
| 2011/0092950 A1 | 4/2011 | Shachar et al. | |
| 2012/0203212 A1 | 8/2012 | Heruth et al. | |
| 2013/0238015 A1 | 9/2013 | Berdahl et al. | |
| 2014/0066830 A1 | 3/2014 | Lad et al. | |
| 2014/0155816 A1* | 6/2014 | Cheng | ................ A61K 38/1825 604/28 |
| 2015/0045766 A1 | 2/2015 | Ludvig et al. | |
| 2015/0088049 A1* | 3/2015 | Anile | .................. A61M 27/006 604/9 |
| 2015/0313761 A1 | 11/2015 | Berdahl et al. | |
| 2016/0074600 A1 | 3/2016 | Miesel | |
| 2019/0282792 A1 | 9/2019 | Wostyn et al. | |

FOREIGN PATENT DOCUMENTS

| | | |
|---|---|---|
| CN | 102018724 A | 4/2011 |
| WO | 9802202 A1 | 1/1998 |
| WO | 200154766 A1 | 8/2001 |
| WO | 2004058337 A1 | 7/2004 |
| WO | 2008105959 A2 | 9/2008 |
| WO | 2011114260 A1 | 9/2011 |
| WO | 2014130777 A1 | 8/2014 |

OTHER PUBLICATIONS

Shang A et al., entitled "Medical artificial cerebrospinal used e.g. for treating subarachnoid hemorrhage, includes sodium chloride, potassium choloride, magnesium chloride, sodium bicarbonate, glucose, disodium hydrogen phosphate, and distilled water," Apr. 20, 2011, Database WPI, XP002751466, 2 pages.

Sun Z et al., entitled "Cerebrospinal fluid displacing equipment for acute clinical treatment of intracranial infections, has machine body fixed with outer side of four-way pipe and connected with connecting pipe and indwelling pipe by transparent pipe," May 9, 2007, Database WPI, XP002751467, 1 page.

Berdahl J P et al., "Intracranial pressure and glaucoma," Current Opinion in Ophthalmology, 2010, 21:106-111.

Uchida K et al., "Possible Harmful Effects on Central Nervous System Cells in the Use of Physiological Saline as Irrigant During Neurosurgical Procedures," Surg Neurol 2004;62:96-105.

Wostyn P et al., "Glaucoma Considered as an Imbalance Between Production and Clearance of Neurotoxins," Invest Ophthalmol Vis Sci., 2014;55:5351-5352.

European Communication issued in Application No. 15790040.8 dated Oct. 1, 2019.

Database WPI, Week 200973, Thomson Scientific, London, GB, AN 2009-Q05844.

Killer, H.E., et al., Is open-angle glaucoma caused by impaired cerebrospinal fluid circulation: around the optic nerve? Clinical and Experimental Ophthalmology 36: 308-311, 2008.

Nucci, C., et al. Glaucoma progression associated with altered cerebral spinal fluid levels of amyloid beta and tau proteins. Clinical and Experimental Ophthalmology 39: 279-281, 2011.

* cited by examiner

THERAPEUTIC APPLICATIONS OF ARTIFICIAL CEREBROSPINAL FLUID AND TOOLS PROVIDED THEREFOR

CROSS-REFERENCE TO RELATED APPLICATIONS

This application is a U.S. national stage entry under 35 U.S.C. § 371 of PCT International Patent Application No. PCT/EP2015/073893, filed Oct. 15, 2015, which claims priority to U.S. Provisional Patent Application No. 62/064,321, filed Oct. 15, 2014 and European Patent Application No. 15163949.9, filed Apr. 17, 2015, the contents of which are incorporated herein by reference in their entirety.

FIELD OF THE INVENTION

The present application one the one hand relates generally to the field of cerebrospinal fluid and its use locally in the brain and/or the spine to increase intracranial pressure and/or cerebrospinal fluid (CSF) turnover. The application relates to Alzheimer's disease and methods and medical devices for the treatment thereof. More particularly, the application provides methods and tools for treating and/or preventing Alzheimer's disease by increasing CSF turnover. The application further relates to glaucoma and methods and medical devices for the treatment thereof. More particularly, the application provides methods and tools for treating and/or preventing glaucoma by increasing intracranial pressure and/or CSF turnover.

The present application also relates generally to the field of medical devices. More particularly, it relates to implantable, pump-assisted devices, capable of infusing fluid (e.g. to infuse artificial cerebrospinal fluid) from a reservoir into a bodily cavity. The application more particularly provides implantable, pump-assisted devices, capable of increasing intracranial pressure and/or CSF turnover. Such devices are of interest in the treatment and/or prevention of glaucoma and in the treatment of Alzheimer's disease and the treatment of neurological disorders in which inflammatory mediators or neurotoxins are involved.

BACKGROUND

The brain and spinal cord are encased within the cranium and vertebral column inside a thin membrane known as the arachnoid. The volume of the intracranial space is on average about 1700 ml including volumes of approximately 1400 ml of brain, approximately 150 ml of intracranial blood; and approximately 150 ml of CSF. CSF circulates within the subarachnoid space and is formed principally by the choroid plexuses, which secrete about 80% of the total volume. The sources of the remainder of CSF are the vasculature of the subependymal regions, and the pia mater. The total volume of CSF is renewed several times per day, so that about 500 ml are produced every 24 hours.

CSF is absorbed through the arachnoid villi, located principally over the superior surfaces of the cerebral hemispheres. Some villi also exist at the base of the brain and along the roots of the spinal nerves. The absorptive processes include bulk transport of large molecules and as well as diffusion across porous membranes of small molecules. See, e.g., Adams et al., (1989) "Principles of Neurology," pp. 501-502.

There are several examples of low-molecular weight proteins or peptides that are known to be present in altered concentrations in CSF of persons suffering from adult-onset dementia of the Alzheimer's type. Alzheimer's disease, the most common type of dementia, is characterized neuropathologically by the presence in the brain of extracellular senile plaques and intracellular neurofibrillary tangles, along with neuronal cell loss. The major component of senile plaques is the low molecular weight peptide beta-amyloid. Neurofibrillary tangles are mainly composed of abnormally phosphorylated tau protein. Studies consistently report decreased levels of beta-amyloid (1-42) in CSF from Alzheimer patients in comparison with healthy subjects. See, e.g., Engelborghs et al., (2008) "Diagnostic performance of a CSF-biomarker panel in autopsy-confirmed dementia," Neurobiol. Aging 29:1143-1159. Beta-2 microglobulin is another example of a low-molecular-weight protein whose concentration in CSF increases with age and reaches high levels in patients with adult-onset dementia of the Alzheimer's type, as reported in Martinez et al., (1993) "Relationship of interleukin-1 beta and beta.sub.2-microglobulin with neuropeptides in cerebrospinal fluid of patients with dementia of the Alzheimer type," J. Neuroimmunology 48: 235-240. Beta-2 microglobulin is associated with amyloid deposits in some tissues of patients on long-term renal hemodialysis. Another substance that accumulates in CSF in patients with adult-onset dementia of the Alzheimer's type is tau, a component of the neurofibrillary tangles found in involved brain tissue. Tau concentrations in CSF are regularly increased in this syndrome with eight fold increases present in half of the patients, as reported in Arai et al., (1995) "Tau in cerebrospinal fluid: a potential diagnostic marker," Ann. Neurology 38: 649-52.

Other neurological diseases are characterized by the presence of inflammatory mediators or neurotoxins, such as central nervous infection, ischemic stroke, subarachnoid hemorrahge, intracerebral hemorrahge, multiple sclerosis, Parkinson's diease traumatic injuries and epilepsy. All of these diseases could theoretically benefit from methods which involve increased CSF turnover and the removal of the concentration of these mediators or toxins.

Previously-known devices have attempted to use filtration techniques to remove or reduce concentrations of harmful proteins from patient body fluids. For example, U.S. Pat. No. 5,334,315 to Matkovich describes a method and device that may be used to remove a body fluid from a patient, treat that fluid to remove an undesirable component, and return the fluid to the patient. Matkovich includes a partial list of the types of deleterious or undesirable substances that may be removed from a fluid, such as proteins, polypeptides, interleukins, immunoglobulins, proteases and interferon. The fluids from which these substances may be removed are described as including CSF, blood, urine and saliva, however, Matkovich does not suggest that his method and device could be used to treat patients suffering from adult-onset dementia of the Alzheimer's type.

Glaucoma is one of the leading causes of irreversible blindness. The most common type of glaucoma is primary open-angle glaucoma (POAG), which is a progressive optic neuropathy with characteristic structural changes in the optic nerve head and corresponding visual field defects. In the glaucomatous optic nerve, cupping of the optic disc reflects a loss of retinal ganglion cell (RGC) axons and a posterior bowing of the lamina cribrosa (forming the anatomic floor of the optic nerve head), accompanied by extensive remodeling of the optic nerve head.

Raised intraocular pressure is recognized as one of the most important risk factors for POAG and lowering it remains the only current therapeutic approach for slowing optic nerve damage and visual field progression in glaucoma patients. Known glaucoma therapies include medicines (e.g., prostaglandin analogues, beta-blockers, carbonic anhydrase inhibitors, and alpha-agonists), laser surgery (e.g., laser trabeculoplasty), and incisional surgery (e.g., trabeculectomy, deep sclerectomy, viscocanalostomy, and glaucoma drainage implants).

Therapy typically starts from the least invasive options, which usually involve the administration of medication. However, the administration of medication often fails for various reasons. Indeed, medicaments for the treatment of POAG typically lower the IOP by at most about 25% to 30%, which can be insufficient. Some glaucoma patients show disease progression despite of the administration of medicaments. Moreover, topical medications for glaucoma can cause side effects such as precipitation of asthma, bradycardia, impotence, and decreased exercise tolerance. There is also a significant problem in compliance with glaucoma medications due to frequent dosing regimens. Incisional surgery is usually required when (topical) glaucoma medication and/or laser surgery fail. However, current incisional surgery techniques for treating glaucoma can lead to various complications including but not limited to choroidal effusion, hypotony maculopathy, suprachoroidal haemorrhage, and bleb infections.

Accordingly, there is a need for an alternative glaucoma treatment which mitigates at least one of the above problems.

A number of implantable pumps have been described in the art. U.S. Pat. Pub. No. 2005/0090549 (Hildebrand et al.) describes a system and method that may be used to treat pain by administering gabapentin to cerebrospinal fluid (CSF) of a patient. The system includes a pump, a catheter and a reservoir containing an effective amount of gabapentin to treat pain in the patient by pumping the gabapentin through the catheter into CSF. U.S. Pat. Pub. No. 201110021469 (Meythaler et al.) describes intrathecal delivery of baclofen to reduce spasticity. Meythaler describes using refillable programmable pump systems that are implantable and provide continuous infusion of baclofen directly into CSF of a patient. However, neither Hildebrand nor Meythaler disclose or suggest a method or system which involves increasing intracranial pressure and/or CSF turnover, nor suggest the use of such a system to treat glaucoma and/or Alzheimer's disease.

SUMMARY OF THE INVENTION

The present disclosure provides a fluid infusion system, and methods of use, that reduce the concentration of or eliminate undesirable proteins from CSF and/or increase intracranial pressure by delivering artificial CSF or CSF-like solutions to the subarachnoid region and replenishing depleted CSF to enhance CSF turnover. In particular, it is believed that administration of artificial CSF or CSF-like solutions enhances CSF turnover. Therefore, by delivering artificial CSF or CSF-like solutions (optionally containing therapeutic agents) to CSF of patients suffering from Alzheimer or other neurological diseases involving inflammatory agents CSF turnover will be enhanced while the therapeutic agents inhibit or eliminate toxic proteins from CSF. Alzheimer patients show low concentrations of beta-amyloid (1-42) in their CSF compared to CSF of age-matched controls, which isinversely correlated with an increase in the amyloid burden in the brain interstitial fluid. This is thought to be due to increased aggregation, fibril and plaque formation, with decreased clearance of these peptides from the central nervous system. See, Silverberg et al., (2003) "Alzheimer's disease, normal-pressure hydrocephalus, and senescent changes in CSF circulatory physiology: a hypothesis," Lancet Neurol 2(8):506-511. Furthermore, beta A-4 amyloid has been shown to be neurotoxic, as described in Bush et al., (1992) "Beta A-4 amyloid protein and its precursor in Alzheimer's disease," Pharmac. Tera. 56: 97-117. In patients suffering from Glaucoma, the administration of artificial CSF or CSF-like solutions increases intracranial pressure and CSF turnover.

Also provided herein is an apparatus for infusing fluid into a body cavity, more particularly the intrathecal or subarachnoid space or the cerebral ventricles, the apparatus comprising:

an implantable pump;
a reservoir containing artificial cerebrospinal fluid;
an infusion catheter having an inlet end coupled to the reservoir, and an outlet end coupled to the implantable pump; and
an inflow catheter having an outlet end configured to be disposed in fluid communication with a body cavity, and an inlet end coupled to the implantable pump;
wherein the implantable pump is configured to selectively move artificial cerebrospinal fluid from the reservoir through the infusion catheter and the inflow catheter to the intrathecal space or the cerebral ventricles at a rate and volume sufficient to increase the intracranial pressure and/or the cerebrospinal fluid turnover in a patient.

In particular embodiments, the apparatus further comprises a microcontroller that controls operation of the implantable pump. In particular embodiments, the apparatus comprises a pressure sensor disposed in communication with the inflow catheter to monitor pressure of cerebrospinal fluid, wherein the microcontroller is configured to activate the implantable pump responsive to an output of the pressure sensor.

In some embodiments, the apparatus may include a microcontroller for controlling the operation of the pump and may be responsive to a pressure sensor and/or a clock. The pressure sensor may provide information regarding the pressure of CSF within the cerebral ventricle. In this manner, the microcontroller may be programmed to pump artificial CSF from the reservoir to the cerebral ventricle only when the pressure of CSF falls below a predetermined value. Alternatively, the microcontroller may be programmed to pump CSF and artificial CSF or CSF-like solutions in predetermined volumes or at predetermined intervals, which may be titrated for each patient.

In particular embodiments the microcontroller is configured to activate the implantable pump so as to ensure a CSF pressure of between 11 and 16 mm Hg, more particularly an ICP of about 15 mm Hg, when measured in the lateral decubitus position. In particular embodiments, the apparatus comprises a feedback mechanism based on said pressure sensor, which ensures that the CSF pressure does not exceed 15 mm Hg. In particular embodiments the microcontroller of the apparatus ensures an increased CSF turnover. In particular embodiments, the CSF turnover is increased to about 4.0 volumes/day.

In particular embodiments of the apparatus envisaged herein, the reservoir contains artificial cerebrospinal fluid. In further particular embodiments, the artificial CSF or CSF-like solutions may comprise one or more therapeutic agents.

In accordance with one aspect of the present invention, the apparatus preferably comprises an implantable electromechanical pump, an infusion catheter, an inflow catheter, a reservoir housing artificial CSF or CSF-like solutions, and a one-way valve. The pump, which in a preferred embodiment may be a positive displacement gear pump, may be located in the chest or abdomen of the patient or external to the patient's body, is configured to transfer fluid from the infusion catheter to the inflow catheter. The infusion catheter is configured to connect the reservoir to the pump. The inflow catheter is configured to connect the pump to a cerebral ventricle or intrathecal space around the spinal cord of a patient. The inflow catheter may be sealed to the cerebral ventricle and/or the spine with a flange. The reservoir may be secured to a holder and worn by the patient like a belt or connected to the infusion catheter like an IV bag. The one-way valve is configured to permit artificial CSF or CSF-like solutions to flow in one direction: away from the infusion catheter and towards the brain or spine. The inflow and infusion catheters may be sealed to the cerebral ventricle and/or the reservoir with a flange. Additionally, the artificial CSF or CSF-like solutions may contain therapeutic agents.

In accordance with another embodiment of the present invention, the reservoir may be implantable under the skin of the patient. The implantable reservoir comprises a septum to be pierced by a needle for refilling of artificial CSF or CSF-like solutions.

In accordance with another aspect of the present invention, the system may comprise a bacterial filter on or within the infusion catheter or the inflow catheter to prevent bacteria from passing through the system to the brain. The bacterial filter may comprise an ultraviolet light module configured to irradiate fluid passing through the filter. Alternatively, some or all of the system components may be coated with or impregnated with antibiotic or antimicrobial coatings or deposits to prevent infection.

In accordance with another aspect of the present invention, the artificial CSF or CSF-like solution delivered to the subarachnoid region of the patient could be absorbed naturally by the arachnoid villi.

The implantable device may include a rechargeable power source, such as a battery. In accordance with another aspect of the present invention, the system may include an extracorporeal controller configured to transmit energy to the implantable components, communicate information to the implantable components, and/or receive data from the implantable components.

Further described herein is an apparatus for infusing artificial cerebrospinal fluid (CSF) to the CSF of a patient, in order to increase the intracranial pressure and/or the cerebrospinal fluid turnover in said patient. The principle of the methods and tools described herein is based on the observation that certain diseases such as but not limited to glaucoma may be associated with a reduced intracranial pressure (ICP). The present inventor proposes the infusion of artificial CSF or CSF-like solutions for the treatment and/or prevention of such diseases. In particular embodiments this can be achieved through an implantable pump, whereby artificial CSF or a CSF-like solution is infused into the intrathecal space or into the cerebral ventricles. The outlet end of the inflow catheter may be disposed in any region of the spine, including the cervical region, the thoracic region, the lumbar region etc. . . . It is envisaged that this provides a therapeutic effect by increasing the ICP and/or the CSF turnover and clearance. In glaucoma, this provides a protective effect for the optic nerve by reducing the trans-lamina cribrosa pressure difference (TLCPD; i.e. intraocular pressure minus intracranial pressure) and/or by enhancing removal of potentially neurotoxic waste products that accumulate in the optic nerve.

Also provided herein are methods of reducing the concentration of undesirable proteins and/or inflammatory agents or neurotoxins, methods for increasing the CSF turnover and/or methods for increasing the intracranial pressure. These methods are of interest in the treatment of different neurological disorders.

In particular embodiments, the methods comprise the steps of (a) providing a reservoir containing artificial cerebrospinal fluid; providing an infusion catheter coupled to the reservoir and the implantable pump and an inflow catheter coupled to an implantable pump; coupling the inflow catheter to a region of a body cavity; and activating the implantable pump to pump the artificial cerebrospinal fluid from the reservoir through the infusion catheter and the inflow catheter to the body cavity at a rate and volume sufficient to replenish, flush, or both, a portion of cerebrospinal fluid with the artificial cerebrospinal fluid to reduce the concentration of undesirable proteins, inflammatory agents or toxins in the cerebrospinal fluid known to contribute to disease. In particular embodiments, the body cavity comprises the arachnoid membrane, the subarachnoid space, one of the lateral ventricles, or the central canal of the spinal cord.

In particular embodiments, the artificial cerebrospinal fluid comprises one or more therapeutic agents.

In further particular embodiments, the methods of reducing the concentration of undesirable proteins and/or inflammatory agents or neurotoxins, methods for increasing the CSF turnover and/or methods for increasing the intracranial pressure further comprise the step of monitoring a pressure of the cerebrospinal fluid within the brain; and deactivating the pump from pumping artificial cerebrospinal fluid from the reservoir to the body cavity when the pressure is greater than a predetermined value. In further particular embodiments, the methods comprise the step of measuring an artificial cerebrospinal fluid volume delivered to the body cavity; and deactivating the pump from pumping artificial cerebrospinal fluid from the reservoir to the body cavity when the artificial cerebrospinal fluid volume is greater than a predetermined value. In particular embodiments, the methods comprise the step of preventing backflow of bacteria through the infusion catheter; irradiating cerebrospinal fluid passing through the infusion catheter with UV light; or coating or impregnating at least one of the implantable pump, infusion catheter, inflow catheter or the reservoir with an antibacterial or antimicrobial agent.

In particular embodiments of the methods, the reservoir is adapted to be implanted within the patient and configured to receive additional artificial cerebrospinal fluid from an external source. In particular embodiments, the methods further comprise the step of providing an extracorporeal controller configured to communicate wirelessly with the pump; and operating the controller to program activation of the pump.

In particular embodiments, the application provides methods for treating Alzheimer's disease or another disease characterized by the presence of undesirable proteins or neurotoxins by administration of artificial CSF or CSF-like solutions.

Accordingly, the application provides for the use of artificial CSF or CSF-like solutions for the treatment of various conditions. In particular embodiments, the application provides artificial CSF or a CSF-like solution for use in the treatment of neurological disorders characterized by the presence of undesirable proteins or inflammatory agents. In particular embodiments, the neurological disorder is Alzheimer's disease. In further particular embodiments, the artificial CSF or CSF-like solution may comprise one or more therapeutic agents which reduce or inhibit the undesirable proteins or inflammatory agents. In particular embodiments, the neurological disorder is selected from central nervous system infection, ischemic stroke, subarachnoid hemorrhage, intracerebral hemorrhage, multiple sclerosis, Parkinson's disease, traumatic injuries (such as cerebrospinal injury or severe traumatic brain injury), amylolateral sclerosis and epilepsy In particular embodiments, the application provides for the use of artificial CSF or CSF-like solutions in the treatment of glaucoma. Thus also provided herein are methods and tools for the prevention and treatment of glaucoma. In particular, the methods comprise increasing intracranial pressure and/or CSF turnover by the administration of artificial CSF or CSF-like solutions.

Provided herein is a method of prevention and/or treatment of glaucoma in a patient which comprises administering artificial CSF or CSF-like solution directly or indirectly into the cerebral ventricles or the intrathecal space of said patient. More particularly the method comprises administering artificial CSF or a CSF-like solution so as to ensure an increase in ICP and/or to increase CSF turnover. In particular embodiments, the method comprises reducing the translamina cribrosa pressure difference (TLCPD; i.e. IOP minus ICP), preferably to a value of about 4 mm Hg, or less such as to a value of 2 or 1 mm Hg. In particular embodiments, the method comprises ensuring a ICP of between 11 and 16 mm Hg, more particularly an ICP of about 15 mm Hg, when measured in the lateral decubitus position. Additionally or alternatively, the methods provided herein comprise ensuring an increase in the total CSF turnover in the patient. The optimal infusion rate of CSF will be dependent on the natural daily absorption of CSF by the patient to allow the body to readily absorb CSF and maintain an adequate ICP. In particular embodiments, the pump may maintain an infusion rate of the fluid in the range of 0.05-0.1 ml/min, 0.1-0.2 ml/min, 0.2-0.42 ml/min, 0.42-0.7 ml/min or even up to 0.7-1.04 ml/min (1.5 L/day). In particular embodiments a turnover is ensured of about 4.0 volumes/day. In particular embodiments, the methods comprise administering the artificial CSF or a CSF-like solution to the intrathecal or subarachnoid space or the cerebral ventricles of said patient by supplementing said patient's CSF with artificial CSF or a CSF-like solution. More particularly this is ensured by way of an apparatus capable of infusing fluid with an implantable pump, more particularly artificial CSF or a CSF-like solution directly or indirectly into the intrathecal space and/or the cerebral ventricles of said patient.

The above and other characteristics, features and advantages of the present invention will become apparent from the following detailed description, which illustrates, by way of example, the principles of the invention.

BRIEF DESCRIPTION OF THE DRAWINGS

The following description of the figures of specific embodiments of the invention is merely exemplary in nature and is not intended to limit the present teachings, their application or uses. Throughout the drawings, corresponding reference numerals indicate like or corresponding parts and features.

DETAILED DESCRIPTION

Figure 1A:
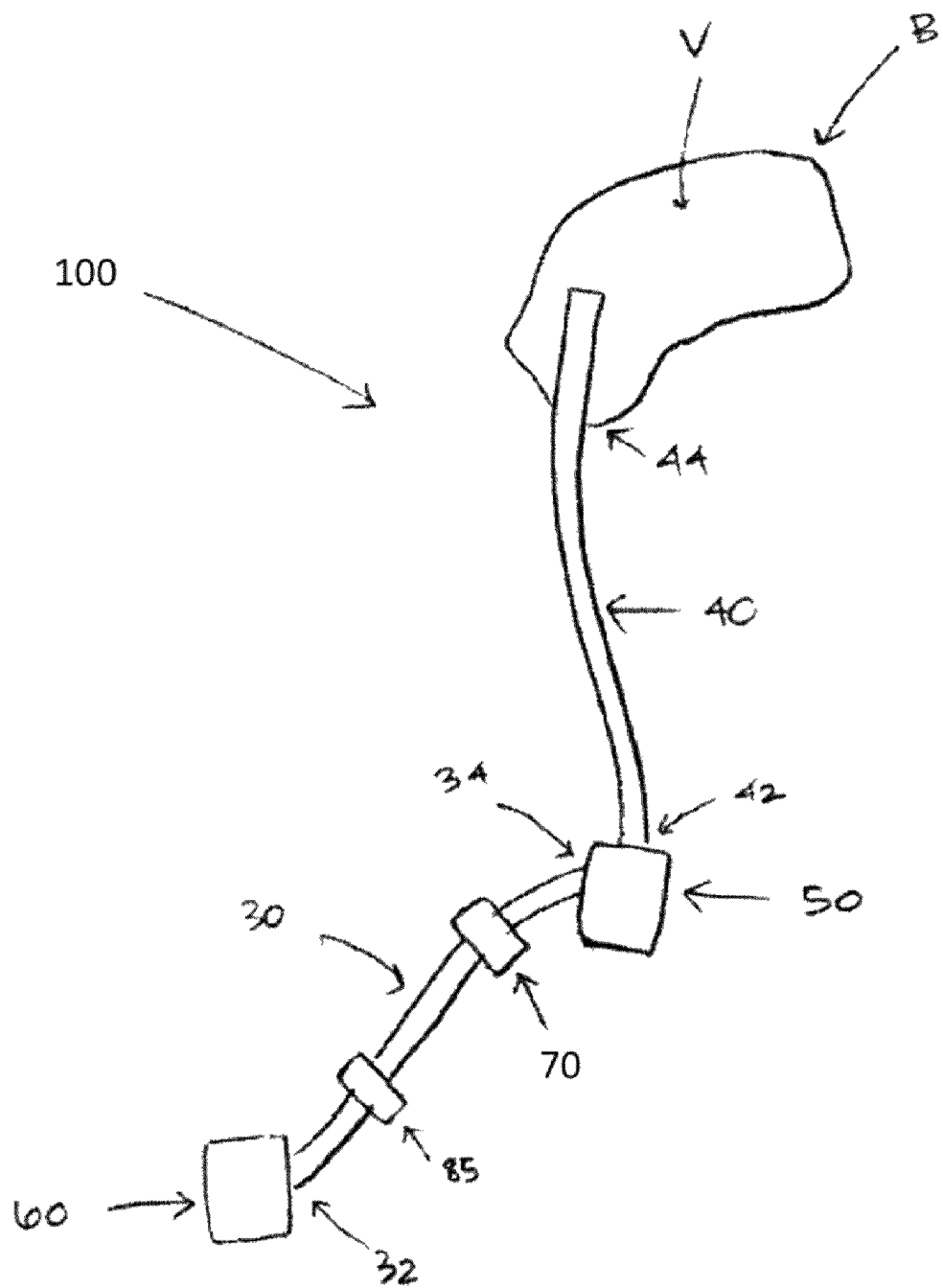
FIG. 1A is a schematic view of the implantable components connected to a brain and an external reservoir according to an embodiment of the invention.

The present invention will be described with respect to particular embodiments but the invention is not limited thereto but only by the claims. Any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited components, elements or method steps also include embodiments which "consist of" said recited components, elements or method steps.

Furthermore, the terms "first", "second", "third" and the "like" in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the features of the claimed embodiments can be used in any combination.

The values as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that each value as used herein is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

CSF flows from the brain ventricles into interconnecting chambers, namely, the cisterns and the subarachnoid spaces (SASs), including the SAS of the optic nerves. The optic nerve, a white matter tract of the central nervous system, is ensheathed in all three meningeal layers and surrounded by cerebrospinal fluid (CSF) in the subarachnoid space (SAS) with a pressure equivalent to intracranial pressure (ICP). Thus, in addition to intraocular pressure (IOP), the optic nerve is exposed to the ICP. The lamina cribrosa, the perforated region of the sclera through which the nerve fibers of the optic nerve pass as they exit the eye, separates these two pressurized regions. The difference between the posteriorly directed IOP and anteriorly directed ICP across the lamina cribrosa is known as the trans-lamina cribrosa pressure difference (TLCPD). The term "intracranial pressure" or "ICP" as used herein thus refers to the pressure of cerebrospinal fluid (CSF) within the skull and thus in the brain tissue and CSF and is also referred to as "CSF pressure". The CSF pressure as assessed by lumbar puncture correlates with ICP, and thus the terms CSF pressure and ICP are used interchangeably. The ICP is built up by the equilibrium between the production and outflow of CSF. If the intracranial compliance is assumed to be constant, the steady-state ICP can be described by a simplified equation: $ICP=I_f \times R_{out}+P_{ss}$, where $I_f$ is CSF formation rate, $R_{out}$ is outflow resistance, and $P_{ss}$ is sagittal sinus pressure. ICP is measured in millimetres of mercury (mmHg). At rest it is normally between 5-15 mmg Hg for an adult when measured by lumbar puncture in the lateral decubitus position. Accordingly, the values of ICP (or CSF pressure) referred to herein refer to values when measured in the lateral decubitus position.

The term "intraocular pressure" or "IOP" as used herein refers to the fluid pressure within the eye. It is measured in millimetres of mercury (mmHg). Normally the IOP ranges from 11 to 21 mmHg with a mean of 16 mmHg.

The "trans-lamina cribrosa pressure difference" or "TLCPD" is the difference between the posteriorly directed IOP and the anteriorly directed ICP across the lamina cribrosa. The pressure drop that occurs across the lamina cribrosa (IOP-ICP) increases with elevation of IOP or reduction of ICP. Indeed, from a mechanical perspective, a similar posteriorly directed force is caused by either a lower pressure on the CSF side of the lamina or a higher pressure on the intraocular side.

A CSF-like solution as used herein refers to a solution that consists essentially of CSF or artificial CSF.

The term "artificial CSF" (aCSF) as used herein refers to a solution that closely matches the electrolyte concentrations of cerebrospinal fluid. Typically, the artificial CSF comprises sodium ions at a concentration of 140-190 mM, potassium ions at a concentration of 2.5-4.5 mM, calcium ions at a concentration of 1-1.5 mM, magnesium ions at a concentration of 0.5-1.5 mM, phosphor ions at a concentration of 0.5-1.5 mM, chloride ions a concentration of 100-200 mM. In one example, the artificial CSF comprises sodium ions at a concentration of 150 mM, potassium ions at a concentration of 3 mM, calcium ions at a concentration of 1.4 mM, magnesium ions at a concentration of 0.8 mM, phosphor ions at a concentration of 1 mM, chloride ions a concentration of 155 mM. aCSFs have been described in the art and include, but are not limited to Elliot's solutions A and B and ARTCEREB™.

Typically where reference is made to the administration of CSF, it is intended to refer to a CSF-like solution or to CSF which is (at least partially) of foreign origin (i.e. not from the patient).

In particular embodiments, the CSF may further comprise one or more therapeutic agents, for example agents for reducing the IOP and/or increasing the ICP. For example specific peptides such as angiotensin have been shown to facilitate the rise in CSF pressure upon CSF infusion.

The term "intrathecal space" also referred to as the subarachnoid space (SAS) is the fluid-filled area located between the innermost layer of covering (the pia mater) of the spinal cord and the middle layer of covering (the arachnoid mater).

The term "undesirable protein" as used herein refers to proteins which are characteristically present in the CSF in certain neurological conditions and are known to be correlated with the disease, such as, for Alzheimer's disease, tau and beta-amyloid. The term "inflammatory agent" as used herein refers to compounds such as cytokines and enzymes which mediate inflammation, such as, but not limited to IL-1beta and tumor necrosis factor (TNF)-alpha, IL-6, IL-8, monocyte chemoattractant protein-1, neutrophil-activating peptide 2, intracellular adhesion molecule-1, soluble Fas, tissue inhibitors of metalloproteinase 1, and matrix metalloproteinases-2 and -9.

The term "neurotoxin" as used herein refers to a compound detrimental to the nervous system that occurs in CSF in certain conditions, such as N-methyl(R)salsolinol in Parkinson's disease and glutamate in certain types of epilepsy.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

The present invention is based on the finding that the intracranial administration of artificial CSF or CSF-like solutions can be beneficial in the treatment of various diseases, more particularly in diseases characterized by the presence of undesirable proteins or inflammatory agents in the CSF and/or by a reduced intracranial pressure. More particularly it has been found that the administration of artificial CSF or CSF-like solutions can ensure an increase in CSF turnover in addition to increasing intracranial pressure in those conditions where this is beneficial. The application therefor provides tools for the intracranial administration of artificial CSF or CSF-like solutions and methods of treatment involving the administration of artificial CSF or CSF-like solutions.

Provided herein are methods and devices for treating Alzheimer's. More particularly provided herein are methods and devices for augmenting the rate of CSF turnover, for the treatment and/or prevention of Alzheimer's disease. More particularly, the methods and tools for the treatment of Alzheimer's provided herein involve the administration of CSF or a CSF-like solution (such as artificial CSF) directly or indirectly to the cerebral ventricles and/or to the intrathecal space around the spinal cord. By delivering CSF or artificial CSF to the subarachnoid region, the rate of CSF turnover and clearance is increased thereby enhancing removal of undesirable proteins accumulating in the CSF in patients suffering from the disease thereby ensuring the treatment of Alzheimer's disease. More particularly, the methods and tools provided herein enhance the removal of proteins such as tau and amyloid-beta which characteristically accumulate in the brain of patients suffering from Alzheimer's disease.

Provided herein are compositions for use in methods of prevention and/or treatment of Alzheimer's disease in a patient in need thereof and corresponding methods of treatment and prevention. More particularly, a composition comprising CSF or a CSF-like solution such as artificial CSF is provided for use in the prevention or treatment of Alzheimer's disease. In particular embodiments, the methods of prevention and/or treatment of Alzheimer's in a patient comprise administering CSF or a CSF-like solution to the intrathecal space or the cerebral ventricles of said patient. More particularly, the artificial CSF is administered to the intrathecal space surrounding the spinal cord. Indeed, the administration of CSF or a CSF-like solution can be done locally, in the cerebral ventricles, but in most embodiments the same effect can be achieved less invasively by infusion more remotely, i.e. intrathecally anywhere along the spinal cord, including the cervical region, the thoracic region, the lumbar region etc. In particular embodiments, the compositions for use in the methods described herein comprise, in addition to artificial CSF one or more therapeutic agents. In particular embodiments, such a therapeutic agent may be an agent which is known to inhibit the aggregation of proteins present in the CSF such as amyloid-beta. Examples of suitable agents capable of inhibiting aggregation of proteins are chaperones, such as but not limited to transthyretin ("TTR"), Cystatin C ("CysC"), beta-trace. Indeed in particular embodiments it is envisaged to add to the artificial CSF of CSF like solution chaperones known to be beta-amyloid-binding chaperones that are reduced in CSF of persons with Alzheimer's disease. For example, lowered CSF levels of transthyretin ("TTR") are associated with beta-amyloid and tau accumulation in patients with Alzheimer's disease. See, Maetzler et al., (2012) "Serum and Cerebrospinal Fluid Levels of Transthyretin in Lewy Body Disorders with and without Dementia," PLoS ONE 7(10): e48042. TTR influences beta-amyloid aggregation and destroys already formed beta-amyloid fibrils. TTR is one of the major beta-amyloid binding and sequestering proteins in human CSF. Patients with Alzheimer's disease are linked to alterations in the structure of choroid plexus in the brain, resulting in a decreased synthesis of TTR in CSF. See, Merched et al., (1998) "Apolipoprotein E, transthyretin and actin in CSF of Alzheimer's patients: relation with the senile plaques and cytoskeleton biochemistry," FEBS Letters 452:225-228. Decreased levels of TTR in CSF lead to accumulation and aggregation of beta-amyloid, beta-amyloid formation, and neurotoxicity.

Cystatin C ("CysC") is another example of a beta-amyloid-binding chaperone whose concentration is decreased in CSF of patients with Alzheimer's disease. Lower levels of CysC may result in decreased ability to inhibit neuronal beta-amyloid aggregation and deposition. CysC protects against neurodegeneration by inhibition of beta-amyloid oligomerization and fibril formation. Experimental, genetic, and clinical data suggest that CysC protects against the development of Alzheimer's disease. See, Zhong et al., (2013) "Alterations of CSF Cystatin C Levels and Their Correlations with CSF Aβ40 and Aβ42 Levels in Patients with Alzheimer's Disease, Dementia with Lewy Bodies and the Atrophic Form of General Paresis," PLoS ONE 8(1): e55328.

Another beta-amyloid-binding chaperone that has been found to be lower in CSF of patients with Alzheimer's disease is beta-trace. Beta-trace is a major endogenous beta-amyloid-binding chaperone in the brain and decreased levels of beta-trace in CSF may be involved in the onset and progression of Alzheimer's disease. See, Kanekiyo et al., (2007) "Lipocalin-type prostaglandin D synthase/beta-trace is a major amyloid beta-chaperone in human cerebrospinal fluid," Proc. Natl. Acad. Sci. USA 104(15):6412-6417. The concept provided herein of administering artificial CSF or CSF like solution allows for the administration of compounds the level of which is dysregulated in the context of a neurological condition.

Provided herein are methods and devices for treating neurological diseases characterized by the accumulation of inflammatory agents and/or neurotoxins. Examples of such diseases include but are not limited to central nervous infection, ischemic stroke, subarachnoid hemorrahge, intracerebral hemorrahge, multiple sclerosis, Parkinson's diease traumatic injuries and epilepsy. More particularly, these deseases are characterized by an accumulation of inflammatory agents such as one or more of, typically two or more of IL-1beta and tumor necrosis factor (TNF)-alpha, IL-6, IL-8, monocyte chemoattractant protein-1, neutrophil-activating peptide 2, intracellular adhesion molecule-1, soluble Fas, tissue inhibitors of metalloproteinase 1, and matrix metalloproteinases-2 and -9. In particular embodiment, the neurological disorder is an acute brain trauma and is characterized by the accumulation of IL-1beta and TNF-alpha. In particular embodiments, the disease is characterized by the accumulation of a neurotoxin such as N-methyl (R)salsolinol, MPTP 6-OHDA in Parkinson's disease and glutamate in certain types of epilepsy, acrolein in multiple sclerosis.

More particularly provided herein are methods and devices for augmenting the rate of CSF turnover, for the treatment and/or prevention of these neurological diseases. More particularly, the methods and tools for the treatment of these neurological diseases involve the administration of CSF or a CSF-like solution (such as artificial CSF) directly or indirectly to the cerebral ventricles and/or to the intrathecal space around the spinal cord. By delivering CSF or artificial CSF to the subarachnoid region, the rate of CSF turnover and clearance is increased thereby enhancing removal of inflammatory agents and/or neurotoxins accumulating in the CSF thereby ensuring the treatment of the disease. More particularly, the methods and tools provided herein enhance the removal of the inflammatory agents and/or neurotoxins which characteristically accumulate in the CSF of patients suffering from these neurological conditions.

Provided herein are compositions for use in methods of prevention and/or treatment of neurological conditions characterized by the presence of inflammatory agents and/or neurotoxins in the CSF in a patient in need thereof and corresponding methods of treatment and prevention. More particularly, a composition comprising CSF or a CSF-like solution such as artificial CSF is provided for use in the prevention or treatment of these neurological conditions. In particular embodiments, the methods of prevention and/or treatment of the neurological condition in a patient comprise administering CSF or a CSF-like solution to the intrathecal space or the cerebral ventricles of said patient. More particularly, the artificial CSF is administered to the intrathecal space surrounding the spinal cord. Indeed, the administration of CSF or a CSF-like solution can be done locally, in the cerebral ventricles, but in most embodiments the same effect can be achieved less invasively by infusion more remotely, i.e. intrathecally anywhere along the spinal cord, including the cervical region, the thoracic region, the lumbar region etc. In particular embodiments, the compositions for use in the methods described herein comprise, in addition to artificial CSF one or more therapeutic agents. In particular embodiments, such a therapeutic agent may be an agent which is known to inhibit the inflammatory agents and/or neurotoxins present in the CSF. Examples of suitable agents capable of inhibiting inflammatory agents are anti-inflammatory drugs such as cyclophosphamide. Examples of agents capable of inhibiting neurotoxins include 3,4-dihydroxybenzalacetone or Rasagiline, inhibitors of 6-OHDA. Examples of suitable agents for inhibiting aggregation are chaperones such as those listed above.

Also provided herein are methods and devices for treating glaucoma. More particularly, provided herein are methods and devices for increasing the ICP (and thus reducing TLCPD) and/or augmenting the rate of CSF turnover, for the treatment and/or prevention of glaucoma. More specifically, the methods and tools for the treatment and prevention of glaucoma described herein involve the administration of CSF or a CSF-like solution (such as artificial CSF) directly or indirectly to the cerebral ventricles and/or to the intrathecal space around the spinal cord. By delivering CSF or artificial CSF to the subarachnoid region, the ICP is increased (or the TLCPD is decreased) and/or the rate of CSF turnover and clearance in the subarachnoid space of the optic nerve is increased (thereby enhancing removal of potentially neurotoxic waste products that accumulate in the optic nerve), thus ensuring the treatment of glaucoma.

Indeed, glaucoma can be prevented or treated from the intracranial compartment side of the lamina instead of, or in addition to, lowering IOP. More particularly, the present inventor has found that reduced ICP contributes to glaucoma via a mismatch in pressures across the lamina cribrosa (TLCPD), such that lowering the TLCPD by manipulation of ICP by infusion of CSF can be used to prevent and/or treat glaucoma. Moreover, the presented treatment allows an enhancement of the rate of CSF turnover which is believed to provide an additional or alternative beneficial effect for the prevention and treatment of glaucoma.

Provided herein are compositions for use in methods of prevention and/or treatment of glaucoma in a patient in need thereof and corresponding methods of treatment and prevention. More particularly, a composition comprising CSF or a CSF-like solution such as artificial CSF is provided for use in the prevention or treatment of glaucoma. In particular embodiments, the methods of prevention and/or treatment of glaucoma in a patient comprise administering CSF or a CSF-like solution to the intrathecal space or subarachnoid space or the cerebral ventricles of said patient. More particularly, the artificial CSF is administered to the intrathecal space surrounding the spinal cord. Indeed, the administration of CSF or a CSF-like solution can be done locally, in the vicinity of the subarachnoid space of the optic nerve, but in most embodiments the same effect can be achieved less invasively by infusion more remotely, i.e. intrathecally anywhere along the spinal cord, including the cervical region, the thoracic region, the lumbar region etc. More particularly the method comprises administering CSF or a CSF-like solution to a patient in need thereof so as to ensure an increase in ICP and/or to increase CSF turnover. In particular embodiments, the method comprises infusing CSF or a CSF-like solution to the intrathecal space or the cerebral ventricles so as to reduce the TLCPD, preferably to less than 4 mm Hg, or even lower to 1 or 2 mmHg. In particular embodiments, the method comprises infusion of CSF or a CSF-like solution such as artificial CSF into the intrathecal or subarachnoid space of a patient to ensure an ICP of between 11 and 16 mm Hg, more particularly up to 15 mm Hg. However, preferably the ICP is not raised above the IOP.

Additionally or alternatively, the methods provided herein comprise ensuring an increase in the total CSF turnover. The turnover of CSF decreases substantially with aging and thus the degree of increase in turnover will need to take into consideration the age of the patient. In a young adult, it is envisaged that the turnover is ideally about 4.0 volumes/day. In particular embodiments, the methods comprise administering the CSF or CSF-like solution to the intrathecal or subarachnoid space of said patient by supplementing said patient's CSF with CSF or a CSF-like solution such as artificial CSF. More particularly this is ensured by way of an implantable apparatus configured for infusing fluid, more particularly CSF or a CSF-like solution into the intrathecal or subarachnoid space of said patient.

In particular embodiments, it is envisaged that the CSF or CSF-like solution may comprise a drug associated with intracranial hypertension.

According to a further aspect, also provided herein is an apparatus such as an infusion pump for infusing CSF or a CSF-like solution into a body cavity, more particularly into the intrathecal or subarachnoid space. The apparatus described herein can be used for the treatment and/or prevention of Alzheimer's disease, specific neurological conditions or glaucoma, more particularly open-angle glaucoma (both the normal-tension and the high-tension form of POAG). Intrathecal infusion pumps are currently widely used for management of chronic pain (morphine pump) and spasticity (baclofen pump). In particular embodiments, the apparatus for infusing fluid into the intrathecal or subarachnoid space of a patient the apparatus comprises an implantable pump, a reservoir for containing artificial cerebrospinal fluid, an infusion catheter having an inlet end coupled to the reservoir, and an outlet end coupled to the implantable pump and an inflow catheter. In particular embodiments the inflow catheter has an outlet end configured to be disposed in fluid communication with said intrathecal or subarachnoid space, and an inlet end coupled to the implantable pump; typically the implantable pump is configured to selectively move artificial cerebrospinal fluid from the reservoir through the infusion catheter and the inflow catheter to the intrathecal or subarachnoid space.

In particular embodiments, the device can be configured to selectively move artificial CSF at a rate and volume sufficient to increase the intracranial pressure and/or the cerebrospinal fluid turnover in a patient. More particularly the rate and volume of CSF infusion are adjusted so as to reduce TLCPD to a value of about 4 mm Hg or less, or even to 2 mm Hg or 1 mm Hg (dependent on the patient). In particular embodiments, the rate and volume of artificial CSF infusion ensures an ICP of between 11 and 16 mm Hg, more particularly up to 15 mm Hg.

The infusion rate ensured by the pump will be determined based on different factors, including the CSF absorption rate of the patient. In particular embodiments, the infusion rate is adjusted to ensure an increased turnover of CSF in the patient. In particular embodiments the pump is configured to ensure a CSF infusion rate in the range of 0.05-0.1 ml/min, 0.1-0.2 ml/min, 0.2-0.42 ml/min, 0.42-0.7 ml/min or even up to 0.7-1.04 ml/min (1.5 L/day). In particular embodiments the infusion rate ensures a turnover of about 4.0 volumes/day.

In particular embodiments, the apparatus comprises a microcontroller that controls operation of the implantable pump. In particular embodiments, the microcontroller regulates the flow of the CSF or CSF-like solution through the inflow catheter.

In further embodiments, the apparatus comprises a flow sensor disposed in communication with the inflow catheter to monitor the volume and flow rate of artificial CSF pumped into the intrathecal space or cerebral ventricles, wherein the microcontroller is configured to activate the implantable pump responsive to an output of the pressure sensor.

The application further provides a combination of the apparatus as described herein and an implantable pressure sensor to monitor intracranial or CSF pressure in the patient. In particular embodiments, the sensor is not physically linked to the rest of the apparatus but can be implanted intrathecally or in the cerebral ventricles. In particular embodiments, the microcontroller of the apparatus is configured to activate or deactivate the implantable pump responsive to an output of the pressure sensor. In particular embodiments, the microcontroller is configured to activate and deactivate the implantable pump so as to ensure a constant intracranial pressure of between 11 and 16 mm Hg, more particularly up to 15 mm Hg. In particular embodiments, the apparatus comprises a feedback mechanism based on the output of the pressure sensor, which ensures that the intracranial pressure does not exceed 15 mm Hg.

Further described herein is the treatment and/or prevention of glaucoma by lowering the TLCPD by increasing the ICP and/or by facilitating CSF turnover which involves the infusion of CSF or a CSF-like solution as described herein. In particular embodiments, this is ensured by the use of an apparatus as described herein. Although the implantation of a CSF pump is a relatively invasive intervention, it provides a worthwhile alternative for or addition to existing therapies, especially for patients for whom non-invasive treatment options are ineffective. In particular embodiments, the TLCPD may be lowered by increasing the ICP.

More particularly, described herein is a method for treating and/or preventing glaucoma, more particularly open-angle glaucoma (both the normal-tension and the high-tension form of POAG) in a patient, comprising administering CSF or a CSF-like solution intrathecally or into the cerebral ventricles of said patient. In particular embodiments, said method comprises providing an apparatus as described herein comprising an implantable pump, a reservoir for containing artificial cerebrospinal fluid, an infusion catheter having an inlet end coupled to the reservoir, and an outlet end coupled to the implantable pump; and an inflow catheter having an outlet end configured to be disposed in fluid communication with said intrathecal or subarachnoid space or the cerebral ventricles, and an inlet and further comprising the steps of:
  providing cerebrospinal fluid or a CSF-like solution in said reservoir;
  coupling the inflow catheter to a region of a body cavity, more particularly an intrathecal space or the cerebral vesicles; and
  activating the implantable pump to pump the cerebrospinal fluid or CSF-like fluid from the reservoir through the infusion catheter and the inflow catheter to the body cavity at a rate and volume sufficient to increase the ICP and/or to increase the CSF turnover.

In particular embodiments, the body cavity is the subarachnoid space, one of the lateral ventricles, or the central canal of the spinal cord.

In particular embodiments, the pump is surgically placed under the skin of the abdomen, and delivers small, CSF or CSF-like fluid through a catheter directly into the CSF locally present. The present inventor has found that pumps may be provided for infusing artificial CSF, in order to increase ICP and/or CSF turnover with the aim of treating conditions such as glaucoma, Alzheimer's and other neurological conditions.

In particular embodiments, the methods and tools described herein are particularly suitable for the prevention and/or treatment of glaucoma. Prevention of glaucoma can be envisaged in patients susceptible to glaucoma such as patients having reduced intracranial pressure and/or increased TLCPD. Examples of risk factors associated with glaucoma include but are not limited to elevated IOP, low ICP, age, gender, high myopica etc. Long term use of topical and systemic steroids produces secondary open-angle glaucoma by causing an increase in IOP.

Indeed, this has been confirmed by the recent observations by Zhao et al. (Physiological Reports 2015, Vol. 3(8): 1-16. Zhao et al report that modification of ICP dramatically altered the magnitude of retinal dysfunction induced by IOP elevation. With higher ICP levels, they observed protection for retinal function against IOP elevation. An ICP of 30 mmHg could completely ameliorate the total loss of retinal function induced by an IOP of 90 mmHg. While the IOP and ICP levels used in that study were deliberately extreme as a proof of concept, this confirms the importance of ICP for retinal physiology."

In particular embodiments, the application envisages determining one or more of the IOP, TLCPD and/or ICP in a patient prior to the administration according to the methods described herein. This step can be ensured in order to determine the suitability of the methods of the invention for the prevention and/or treatment of glaucoma. Additionally or alternatively it can be used to determine the optimal infusion rate of CSF.

Methods applied for non-invasive estimation of ICP are known in the art and include transcranial Doppler ultrasonography, tympanic membrane displacement, ophthalmodynamometry, measurement of the orbital CSF space around the optic nerve, two-depth transcranial Doppler technology and others. Two-Depth Transorbital Doppler (TDTD) measurement of intracranial pressure quantitative absolute (ICP) value relies on the same fundamental principle as used to measure blood pressure with a sphygmomanometer. The TDTD method uses Doppler ultrasound to translate pressure balance principle of blood pressure measurement with a sphygmomanometer to the measurement of ICP. The ophthalmic artery (OA), which is a vessel with intracranial and extracranial segments, is used as pressure sensor and as a natural pair of scales for absolute ICP value in mmHg or mmH$_2$O measurement. Blood flow in the intracranial OA segment is affected by intracranial pressure, while flow in the extracranial (intraotbital) OA segment is influenced by the externally applied pressure (Pe) to the eyeball and orbital tissues.

Exemplary Infusion System According to the Invention

Figure 1B:
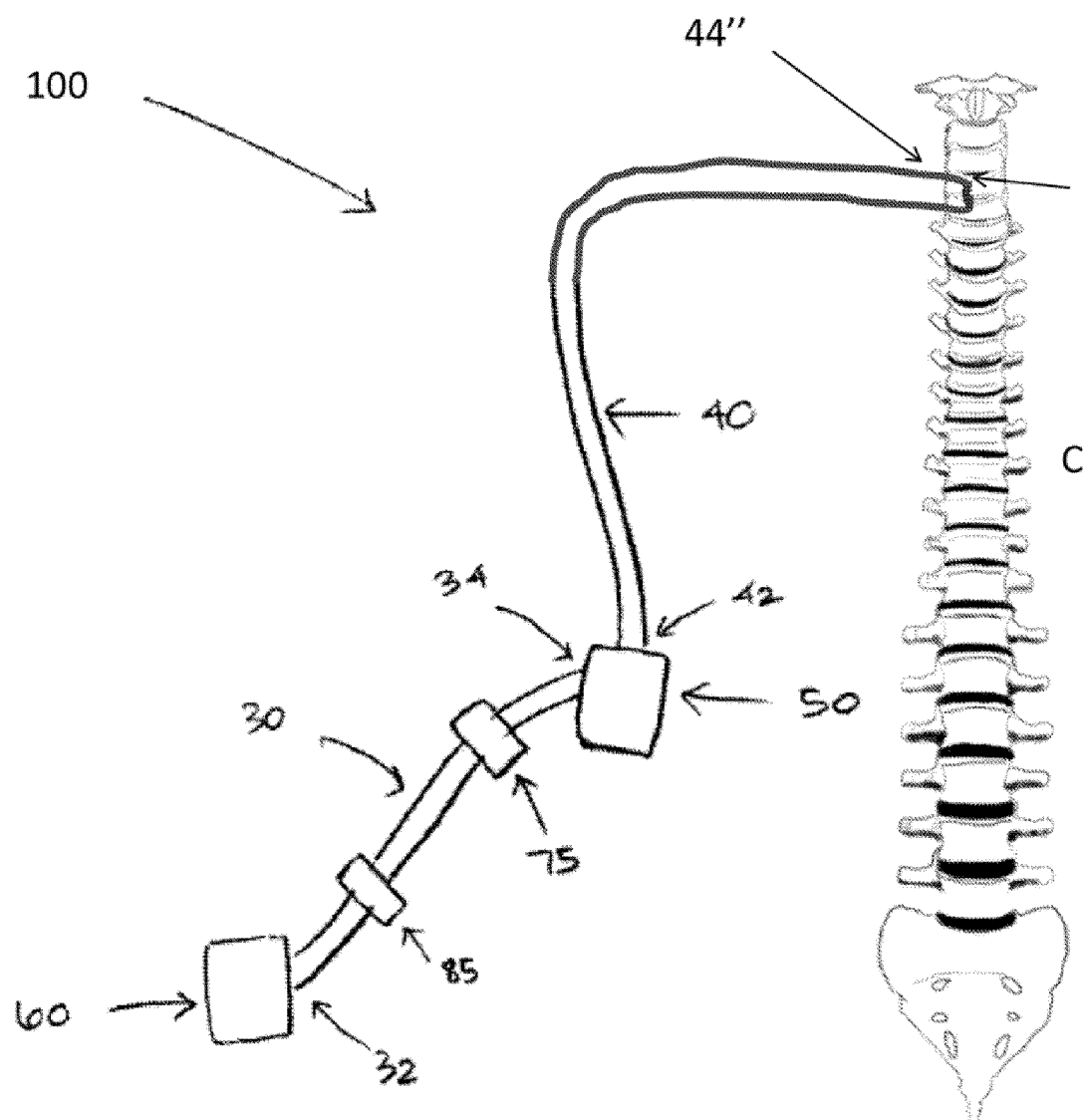
FIG. 1B is a schematic view of the implantable components connected to a spinal cord and an external reservoir according to an embodiment of the invention.

In FIG. 1A, infusion system 100 comprises infusion catheter 30 connecting reservoir 60 to pump 50, and inflow catheter 40 connecting pump 50 to cerebral ventricle V of brain B of the patient. While FIG. 1A depicts inflow catheter 40 connecting pump 50 to the patient's brain, one skilled in the art would understand that inflow catheter may be similarly connected to another source of CSF including the patient's spine. System 100 provides a unidirectional path for movement of artificial CSF to flow from reservoir 60 to brain B. Referring to FIG. 1A, artificial CSF from reservoir 60 is drawn into inlet end 32 of infusion catheter 30 by pump 50, and expelled through outlet end 44 of outlet catheter 40 into brain B. Alternatively, outlet end 44" may be disposed in the spinal cord as depicted in FIG. 1B. While the outlet end of the inflow catheter is illustratively disposed in the cervical region of the spine, the outlet end of the inflow catheter may be disposed in any region of the spine, including the lumbar region, the thoracic region, etc. One-way valve 70 is positioned along infusion catheter 30 or inflow catheter 40 to prevent back flow of fluid through system 100. Optional bacterial filter 85 may be positioned along infusion catheter 30, inflow catheter 40, or disposed within the housing of pump 50 to destroy harmful bacteria and prevent bacteria from migrating through system 100 to brain B. Alternatively, or in addition, the components of system 100 may be coated or impregnated with an antibacterial or antimicrobial coating to reduce the risk of infection.

Figure 1C:
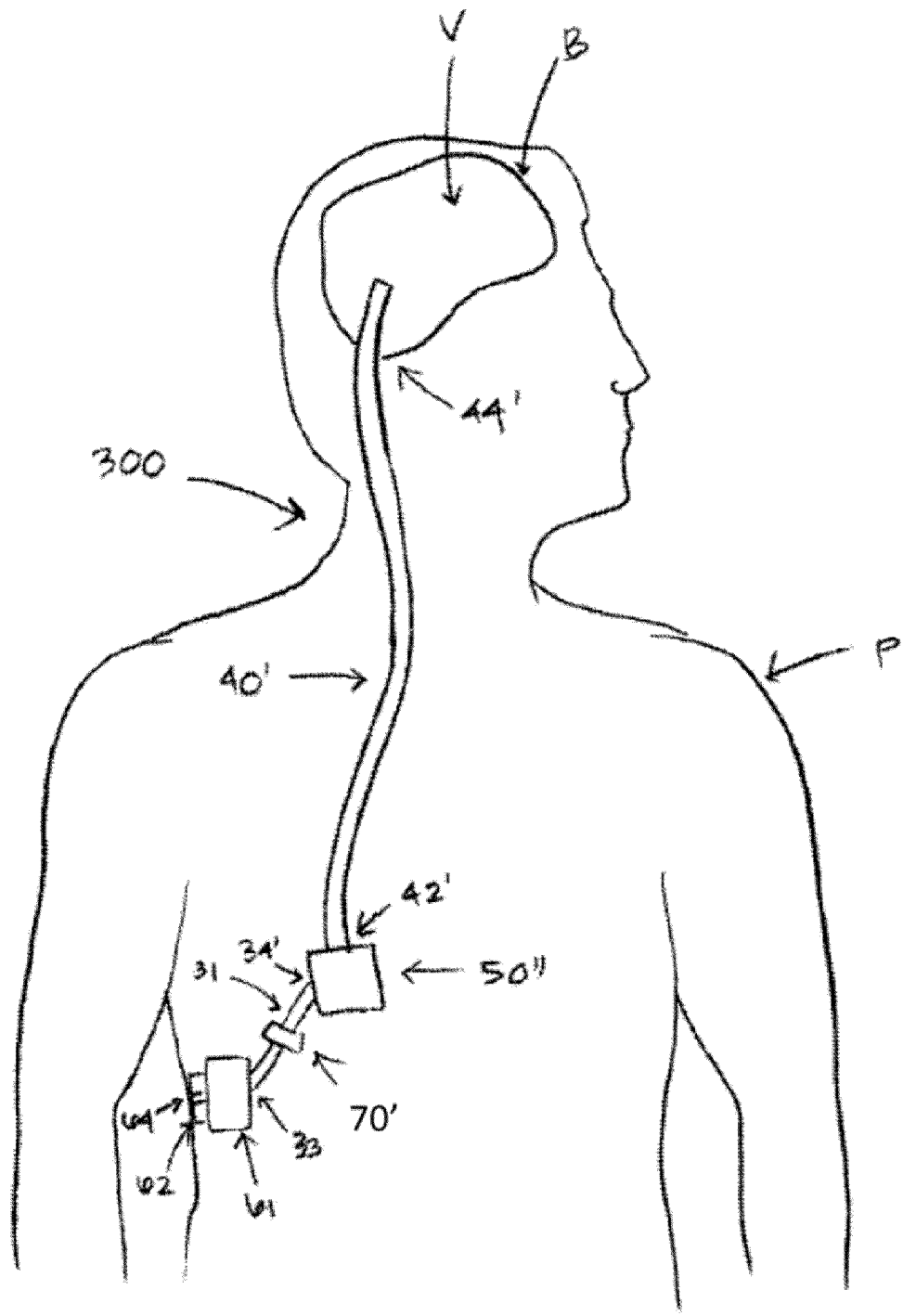
FIG. 1C is a schematic view of the implantable components connected to a brain and an implantable reservoir according to an embodiment of the invention.

In particular embodiments, infusion catheter 30, inflow catheter 40, and pump 50 may be implanted separately and then coupled together during implantation of pump 50. For example, catheters 30 and 40 may be separately implanted using a tunneling technique to place outlet end 44 of inflow catheter 40 in communication with a different region of the source of CSF. Outlet end 34 of infusion catheter 30, and inlet end 42 of inflow catheter 40 then may be lead to the site for implantation of pump 50, and coupled to the pump prior to implantation. Reservoir 60 may be secured to a holder such as a belt and worn by the patient allowing the patient to transport the reservoir with mobility or reservoir 60 may be connected to infusion catheter 30 like an IV bag. Alternatively, reservoir 61 may be implantable under the skin of patient P, as depicted in FIG. 1C. In an alternative embodiment, one or more of infusion catheter 30, inflow catheter 40, and pump 50 may be coupled together prior to implantation and implanted together.

Referring to FIG. 1C, reservoir 61 also may be implanted separately from infusion catheter 31, inflow catheter 40' and pump 50". For example, inlet end 33 of infusion catheter 31 is placed in communication with reservoir 61 prior to being coupled to pump 50". Reservoir 61 may be configured in any form suitable for placement under the skin so that it is capable of receiving artificial CSF. For example, reservoir 61 may comprise septum 62 fluidly connected to reservoir 61 and/or port opening 64 to receive artificial CSF via a syringe. Conveniently, the form of reservoir 61 may be similar or identical to conventional implantable reservoirs of the type used for delivering a liquid therapeutic substance to a delivery site, such as that described in U.S. Pat. No. 8,348,909 to Haase, the full disclosures of which are incorporated herein by reference. Suitable reservoirs that may be incorporated into systems constructed according to the present invention are available from commercial suppliers, such as Medtronic PS Medical, Goleta, Calif.

As will be understood, catheters 30 and 40 comprise biocompatible materials, and may be provided in standard lengths or a single length that may be cut to size to fit a particular patient's anatomy during the implantation procedure. Each connection in system 100 preferably includes a fluid-tight seal and may be accomplished through any variety of methods as known to one of skill in the art.

Infusion catheter 30 and inflow catheter 40 may be formed from a resilient material, such as implant grade silicone or reinforced silicone tubing. The catheters may be reinforced along a portion of their length or along the entire length of the catheters. Reinforcement of the tubing may be accomplished via ribbon or wire braiding or lengths of wire or ribbon embedded or integrated within or along the tubing. The braiding or wire may be fabricated from metals such as stainless steels, superelastic metals such as nitinol, or from a variety of suitable polymers.

Outlet end 44 of inflow catheter 40 is configured to be disposed in fluid communication with a source of CSF. For example, outlet end 44 may be positioned within CSF of the intrathecal space or in a cerebral ventricle V of brain B of patient P. More specifically, outlet end 44 may be positioned within the arachnoid membrane, the subarachnoid space, or one of the lateral ventricles. The ventricles form a group of interconnected cavities that are located within the cerebral hemispheres and brain stem. These ventricles or spaces are continuous with the central canal of the spinal cord and are similarly filled with CSF that may be absorbed and replenished by the body of the patient. Alternatively, artificial CSF may be infused by system 100 to replenish, flush, or both, CSF in these same spaces.

Outlet end 44 may be configured in any form suitable for placement within brain B so it is capable of depositing artificial CSF in a cerebral ventricle. Conveniently, the form of outlet end 44 may be similar or identical to conventional ventricular catheters of the type used for draining CSF for treating hydrocephalus, such as those described in U.S. Pat. No. 5,385,541 to Wolff and U.S. Pat. No. 4,950,232 to Ruzicka, the full disclosures of which are incorporated herein by reference. Additionally, the form of outlet end 44 may be similar or identical to conventional ventricular catheters of the type used for delivering artificial CSF for treating pain or spasticity, such as those described in U.S. Pat. Pub. Nos. 2005/0090549 to Hildebrand and 201110021469 to Meythaler, respectively, the full disclosures of which are incorporated herein by reference. Suitable ventricular catheters that may be incorporated into systems constructed according to the present invention are available from commercial suppliers, such as Medtronic PS Medical, Goleta, Calif.

Figure 3:
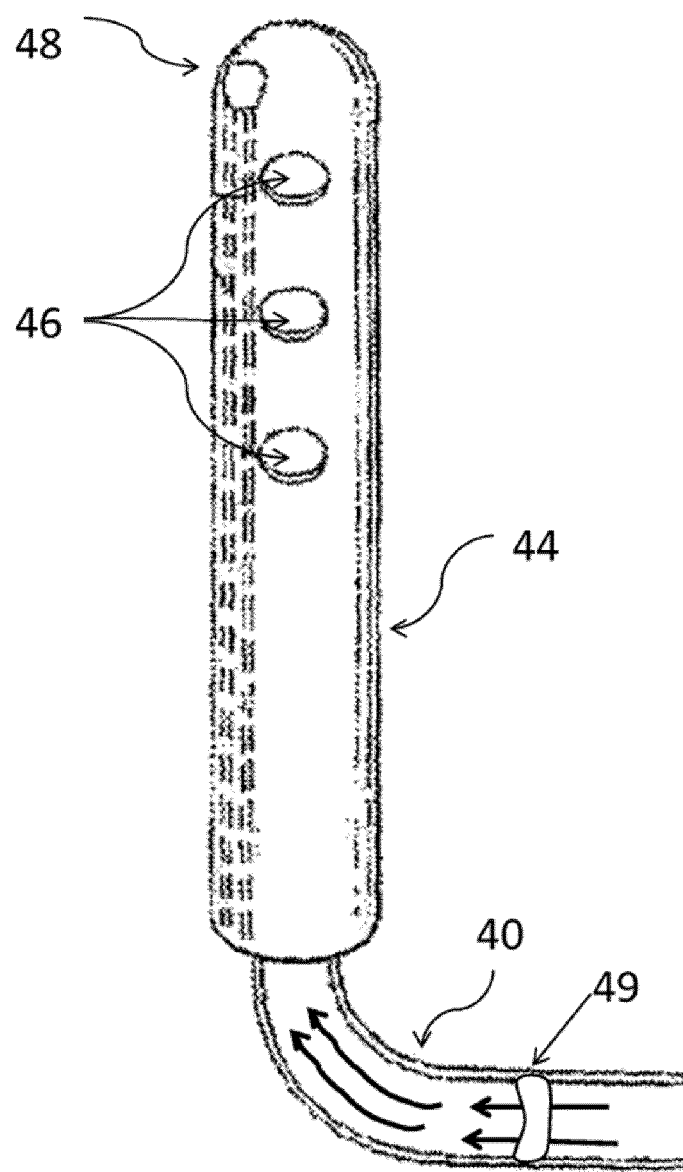
FIG. 3 is a perspective view of the outlet end of the inflow catheter of the fluid infusion system according to an embodiment of the invention.

Referring to FIG. 3, one example of outlet end 44 of inflow catheter 40 is described. Outlet end 44 may include multiple perforations or holes 46, which preferably do not extend more than about 1 to 1.5 cm from the tip. Although a particular outlet hole arrangement is shown, other arrangements may be used without departing from the scope of the invention. Outlet end 44 preferably comprises biocompatible material suitable for implantation in the patient such as implant grade low bending modulus material that is generally kink resistant, such as silicone or reinforced silicone, or medical shunt tubing. The tubing may have an outer diameter of about 2.0 mm and an inner diameter of about 0.5-1.5 mm. Outlet end 44 further may comprise a flange configured to promote sealing to the brain, to allow inflow catheter 40 to pass into the cerebral ventricles without fluid leakage.

One or more sensors may be integrated into system 100 for detecting and/or indicating a variety of fluid and/or pump parameters to other components of the system or to the physician or patient. For example, outlet end 44 may further include, or be in communication with, pressure sensor 48, such as a pressure transducer, configured to monitor CSF pressure or ICP, for instance at outlet end 44 of outlet catheter 40, as shown in FIG. 3. Pressure sensor 48 may be disposed in CSF within cerebral ventricle V of brain B and located in the vicinity of the tip of outlet end 44 of outlet catheter 40. Pressure sensor 48 need not be physically connected to the rest of the apparatus but may be in wireless connection therewith. Pressure sensor 48 may be used to monitor the ICP and ensure that the ICP is sufficiently high as to obtain a normal TLCPD. Additionally, the pressure sensor may be used to monitor the ICP and ensure that the ICP is not increased to a level that increases the risk of subdural hematomas or hydrocephalus and midline shifts or that destabilizes the pressure in the ventricles.

Figure 2:
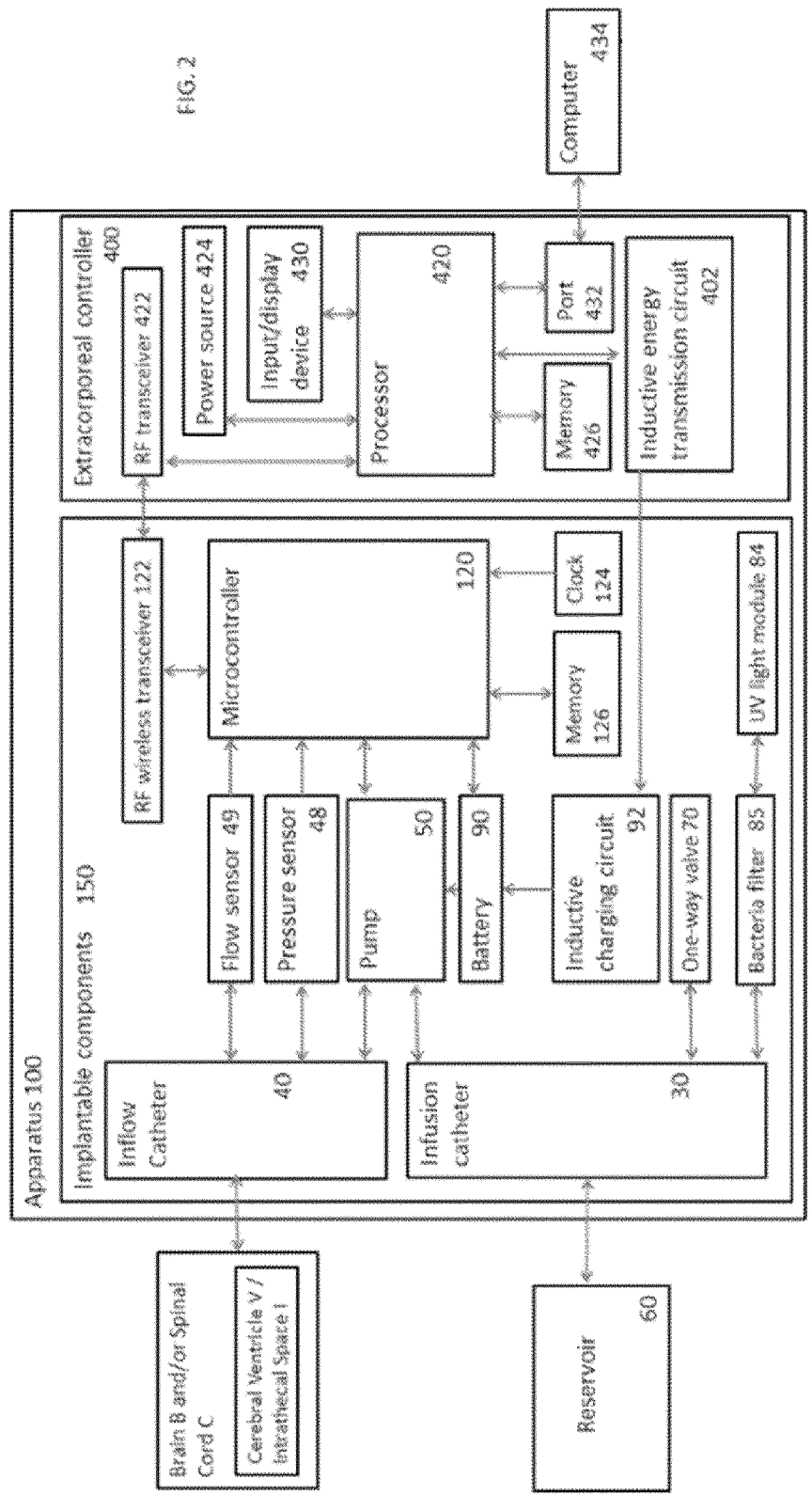
FIG. 2 is a schematic diagram of a fluid infusion system according to an embodiment of the present invention.

In order to ensure a suitable ICP (and TLCPD), pressure sensor 48 further may be configured to provide an output that is used to control operation of pump 50. For example, pressure sensor 48 may be configured to send a signal to microcontroller 120, in response to sensing a pressure above or below a certain threshold or predetermined amount. Microcontroller 120 may be configured to control the operation of pump 50 (as shown in FIG. 2) by activating or stopping the pump from pumping artificial cerebrospinal fluid from the reservoir to the brain in response to the output of pressure sensor 48. More specifically, microcontroller 120 may activate and stop pump 50 as to obtain an ICP between 11 and 16 mm Hg, preferably up to 15 mm Hg.

In particular embodiments, microcontroller 120 may activate and stop pump 50 as to reduce the TLCPD (i.e. IOP minus ICP), preferably to a value of about 4 mm Hg, preferably even less than 4 mm Hg, such as 2 mm Hg or 1 mm Hg. TLCPD may be determined or estimated based on the ICP as measured by a sensor as described above and an (average) IOP value obtained via a prior measurement, e.g. via tonometry as known in the art.

Inflow catheter 40 may further include flow sensor 49 to detect, measure, and/or monitor the volume and flow rate of artificial CSF pumped into the intrathecal space surrounding the spinal cord and/or into the cerebral ventricles. Flow sensor 49 also may be configured to send a signal to microcontroller 120 regarding the volume and flow rate in order to control pump 50. Flow sensor 49 also may be used to ensure that system 100 is operating properly after implantation and during use.

In a preferred embodiment, microcontroller 120 coordinates and controls operation of the components of system 100. For example, microcontroller 120 may use output signals from pressure sensor 48 and flow sensor 49 to control pump 50 by turning the pump on or off or increasing or decreasing the pump speed (and therefore the fluid flow rate). As a further example, microcontroller 120 may stop pump 50 from pumping artificial CSF from the reservoir into the intrathecal space surrounding the spinal cord and/or into the cerebral ventricles when a specific volume of artificial CSF has been pumped, unless CSF pressure or ICP is less than a threshold pressure.

Microcontroller 120 may be configured to send a signal to power source 424 coupled to pump 50 to indicate when to provide or stop power to pump 50 responsive to output used within system 100 to send signals between the components, such as pressure sensor 48, flow sensor 49, pump 50, and microcontroller 120. Microcontroller 120 further may include memory 126 to record operation of system 100 and/or record a specific algorithm used to infuse the artificial CSF.

Figure 4A:
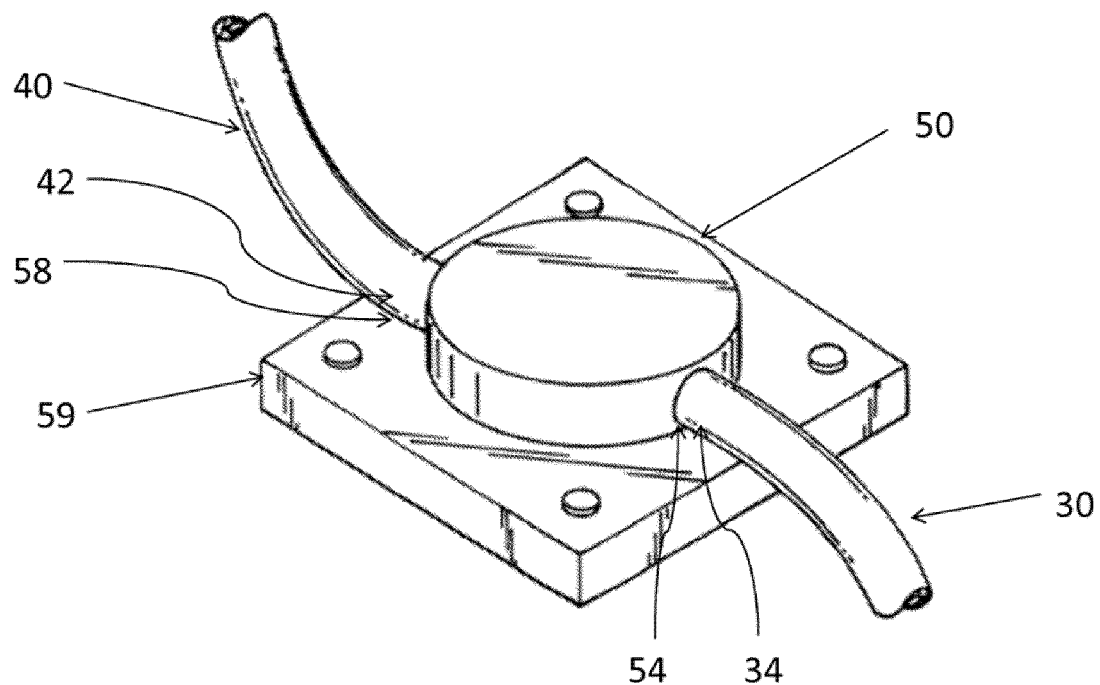
FIGS. 4A and 4B are, respectively, a perspective view of the implantable pump for use in the fluid infusion system and a cross-sectional view of an implantable pump mechanism for use within the fluid infusion system according to an embodiment of the invention.

As shown in FIG. 4A, outlet end 34 of infusion catheter 30 is connected to, or coupled with inlet port 54 of pump 50. Outlet port 58 of pump 50 then is connected to inlet end 42 of inflow catheter 40. Pump 50 is configured to control the flow rate and the infusion rate of the fluid (e.g. artificial CSF) being deposited by system 100. More specifically, pump 50 controls the flow rate from reservoir 60 through infusion catheter 30 and into inflow catheter 40.

FIG. 4A shows an embodiment of implantable pump 50 connected to infusion catheter 30 and inflow catheter 40. Pump 50 preferably comprises a battery-powered electromechanical pump. Further, pump 50 may be a positive displacement gear pump as described in U.S. Pat. Pub. No. US 201210209165 to Degen, the entire contents of which are incorporated herein by reference. Alternatively, pump 50 may be a diaphragm pump, piston pump, rotary pump, peristaltic pump, screw pump, or any other suitable pump configuration. Pump 50 also may be remotely operated as is known in the art. Pump 50 preferably is disposed in a housing manufactured from a suitable biocompatible material, and may include base 59 having suture holes that permit the pump to be fixed to a portion of the patient's anatomy, e.g. within the thorax or peritoneum.

Figure 4B:
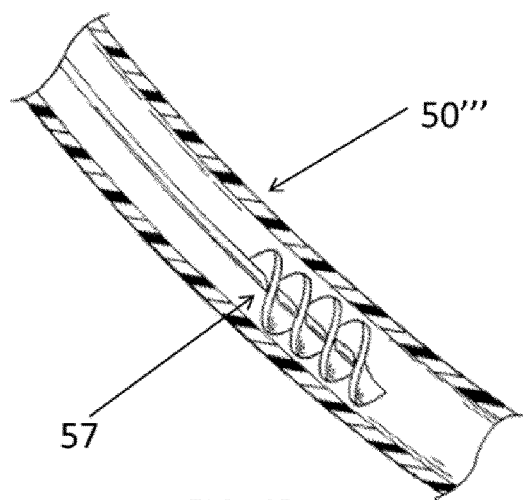

FIG. 4B illustrates an alternative screw pump arrangement, suitable for use in system 100, where screw shaft 57 is mounted for rotation within pump 50''' and the drive is disposed in a hermetically sealed package mounted to the conduit exterior. The drive may be coupled to the screw shaft 57 with a gear transmission as would be apparent to one of ordinary skill in the art. Other screw pump configurations also may be useful, such as those disclosed in U.S. Pat. No. 4,857,046 to Stevens et al. or U.S. Pat. No. 5,372,573 to Habib.

Pump 50 may be placed and secured anywhere between infusion catheter 30 and inflow catheter 40, although it is preferably implanted at site that provides good accessibility to the surgeon and provides some protection for the device, once implanted. For example, pump 50 may be implanted within the chest or abdomen of the patient. More specifically, pump 50 may be placed in the thoracic cavity and positioned in the lateral mid-thorax near the axillary line and on the under surface of a rib, and may be held in place with sutures to the periosteum.

Referring now to FIG. 2, pump 50 in a preferred embodiment is controlled by microcontroller 120. Pump 50 may operate continuously or periodically to deposit CSF in the intrathecal space surrounding the spinal cord and/or into the cerebral ventricles. For example, pump 50 may operate according to a schedule, time, or program, operate on demand, or operate according to the sensed parameters, such as CSF pressure (ICP) or the volume pumped. Microcontroller 120 may use the output of pressure sensor 48 and/or flow sensor 49 to control the flow rate provided by pump 50, as discussed previously. Alternatively or additionally, pump 50 may maintain an infusion rate of CSF at a rate selected to be equal to the natural daily absorption of CSF by the patient to allow the body to sufficiently absorb CSF and maintain an adequate intracranial pressure. Pump 50 may maintain an infusion rate of the fluid in the range of 0.05-0.1 ml/min, 0.1-0.2 ml/min, 0.2-0.42 ml/min, 0.42-0.7 ml/min or even up to 0.7-1.04 ml/min (1.5 L/day).

Microcontroller 120 may include clock 124 to control pump 50. For example, microcontroller 120 may be programmed to activate the pump periodically in response to clock 124 and to pump a predetermined amount of artificial CSF from reservoir 60 to cerebral ventricle V. The predetermined amount may be based on average or specific CSF infusion rates with respect to particular times of day, or may be specifically titrated for a particular patient.

As depicted in FIGS. IA and 4, infusion catheter 30, which may be similar in design to inflow catheter 40, connects reservoir 60 to pump 50. In particular, outlet end 34 of infusion catheter 30 is coupled with inlet port 54 of pump 50.

Inlet end 32 of infusion catheter 30 is configured to be coupled to reservoir 60, so that artificial CSF is drawn through inlet end 32 into pump 50. As described above, reservoir 60 may be external to the patient's body or implanted under the skin of the patient with means for receiving additional artificial CSF.

One-way valve 70 may be positioned along infusion catheter 30 or inflow catheter 40 to provide unidirectional flow of artificial CSF within system 100. More specifically, one-way valve 70 allows the fluid to flow in only one direction: from the reservoir to the brain or spine. This prevents any backflow to the reservoir of harmful proteins from the brain. One-way valve 70 may be located within or on infusion catheter 30 or inflow catheter 40 or more preferably, may be housed within pump 50.

Figure 5A:
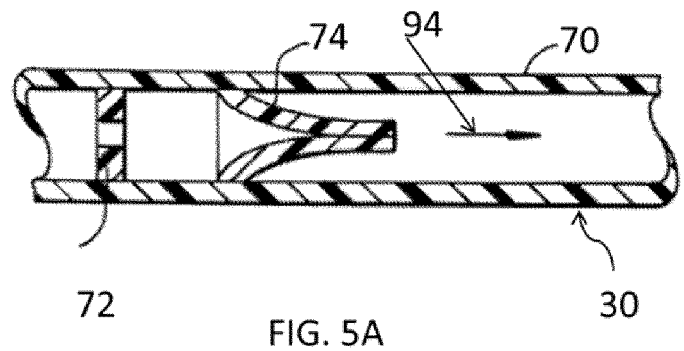
FIGS. 5A, 5B, and 5C illustrate cross-sectional views of alternative one-way valves to control the direction of fluid flow within the fluid infusion system according to an embodiment of the invention.
Figure 5B:
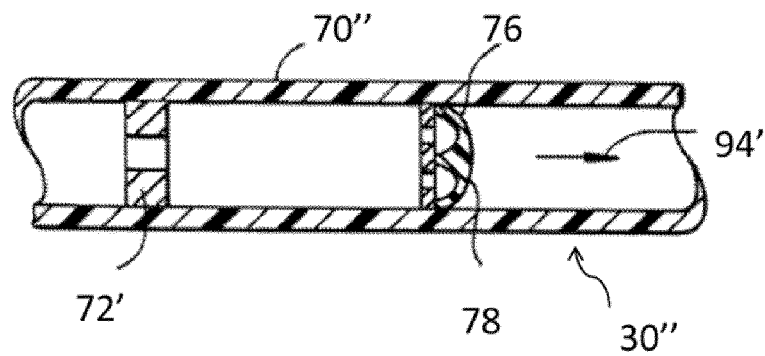
Figure 5C:
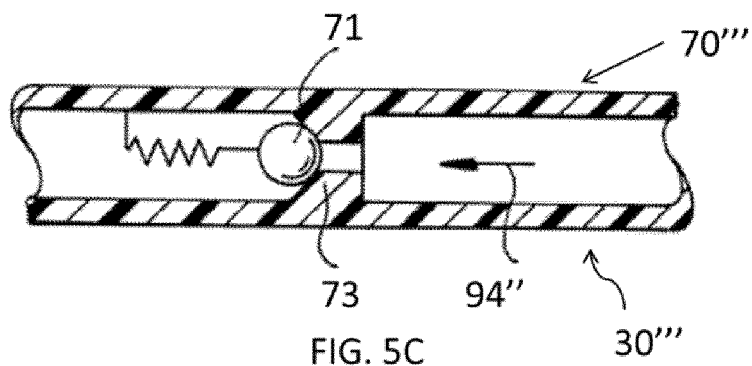

Examples of one-way valves suitable for use in system 100 are shown in FIGS. 5A-5C. In each of the examples, fluid may flow freely in the direction of arrow 94. However, fluid flow opposite to the direction of arrow 94 will force one-way valve 70 to close, thereby preventing backflow. In order to re-open one-way valve 70, sufficient pressure in the direction of arrow 94 must be provided, thus ensuring that fluid moves only in the correct direction.

As shown in FIG. 5A, one-way valve 70 may comprise orifice plate 72 in series with one-way valve 70, illustratively, duck-bill valve 74. Both orifice plate 72 and duck-bill valve 74 may be mounted within infusion catheter 30, inflow catheter 40 or the housing of pump 50. Flow in the direction of arrow 94 will open duck-bill valve 74 and permit fluid flow through infusion catheter 30 and inflow catheter 40. One-way valve 70 alternatively or additionally may comprise a variety of other flow restrictive elements, such as a multiple orifice plate, a filter element, or any other discrete element or combination of elements that may provide a flow resistance capable of yielding the flow rates described herein. FIG. 5B depicts another embodiment of one-way valve 70" comprising orifice plate 72' in series with umbrella valve 76. Umbrella valve 76 includes an elastomeric membrane 78 that opens under pressure to permit flow in the direction of arrow 94'. FIG. 5C depicts yet another embodiment of one-way valve 70''' comprising spring-loaded ball valve 71 disposed in valve seat 73. Valve seat 73 also serves as an orifice to limit flow through the assembly and control the direction of the fluid flow. Flow in direction of arrow 94" will open ball valve 71 and permit flow through the orifice defined by valve seat 73.

In the above cases, the orifice may be selected to provide a desired flow rate when the patient is in a vertical position. One-way valve 70 will be implanted within the patient with a known orientation, usually vertical, in order to provide a known pressure head of artificial CSF onto orifice 72 or 73. This pressure will be sufficient to open the associated one-way valve 70 and flow will be established when the patient is in an upright position. Suitable orifice diameters in the range from 0.03 mm to 0.4 mm, preferably from 0.1 mm to 0.2 mm, for orifices having a thickness in the range from 0.001 mm to 100 mm, preferably from 1 mm to 5 mm, in order to establish average hourly flow rates in the range from 0.5 ml/hour to 15 ml/hour, preferably 1 ml/hour to 3 ml/hour.

A bacterial filter 85 may be included between inlet end 32 of infusion catheter 30 and outlet end 44 of inflow catheter 40 to prevent bacteria from migrating through system 100 to the patient's brain as depicted in FIG. 1A. Although one-way valve 70 is located along infusion catheter 30 or inflow catheter 40, bacterial filter 85 may be desirable to further prevent bacteria from reaching the brain in the event of malfunction of pump 50. Bacterial filter 85 may be incorporated in the housing of pump 50, and may include ultraviolet ("UV") light module 84 configured to irradiate artificial CSF and destroy bacteria passing within infusion catheter 30 and inflow catheter 40. Optionally, bacterial filter 85 may be replaced by antibiotic or antimicrobial coatings disposed on or impregnated within some or all of the components of system 100.

Referring again to FIG. 2, system 100 may include extracorporeal controller 400 that communicates wirelessly with implantable components 150. Extracorporeal controller 400 may provide power to implantable components 150 and/or control activation of the implantable components, such as pump 50.

Implantable components 150 may be powered by battery, or alternatively by a super-capacitor, or other energy storage device. In a preferred embodiment, the power/energy source may be rechargeable. For example, battery 90 may be coupled to implantable inductive charging circuit 92 configured to receive energy from inductive energy transmission circuit 402 of extracorporeal controller 400.

Microcontroller 120 may be coupled to a first transceiver, such as radio frequency (RF) wireless transceiver 122. Extracorporeal controller 400 may be coupled to a second transceiver, such as RF transceiver 422. RF wireless transceiver 122 and RF transceiver 422 may bi-directionally communicate information, such as the operation of the pump, CSF pressure or ICP, and/or the desired infusion rate of the artificial CSF. For example, microcontroller 120 may receive programmed instructions from extracorporeal controller 400 relating to pump activation intervals, targeted volumes of CSF to be pumped and desired flow rates. Additionally, extracorporeal controller 400 may receive data or information from microcontroller 120 relating to pump activation periods, measured pressures, and actual volumes of artificial CSF pumped through inflow catheter 40.

Extracorporeal controller 400 preferably includes processor 420 to coordinate and control its various components and functions. Extracorporeal controller 400 further may include power source 424 to power the extracorporeal controller (and potentially also implantable components 150), and may comprise a battery or an electrical outlet. Extracorporeal controller 400 further may include memory 426 to record information, such as the information received from implantable components 150 or a specific algorithm to convey to the implantable components regarding the infusion of artificial CSF to the brain.

In order for the patient or the physician to enter information into system 100 or for system 100 to display information, extracorporeal controller 400 preferably includes input/display device 430 and/or port 432 to connect to computer 434, such as a laptop computer. Input/display device 430 may include indicators or a control interface to control system 100 and display detailed information about the system. Extracorporeal controller 400 optionally may wirelessly conveyor receive information from computer 434, such as whether system 100 is properly functioning, the current (and past) CSF pressures, the volume of artificial CSF injected, the current (and past) flow rate of artificial CSF through the system, and/or whether pump 50 is currently activated. This information may be conveyed to the patient or physician as a visual message or indicator signal, such as a light or audible signal, that is initiated once pump 50 has been activated. Computer 434 may optionally provide power to extracorporeal controller 400.

Example 1

Short- and Long-Term CSF Infusion Experiments in an Animal Model of Alzheimer's Disease A project approval of the Dutch regulatory instances is obtained for all animal experiments described below. The effects of CSF infusion on Aβlevels are studied at a timescale of 72 hours, because the steady state Aβlevels are reached within a few hours. This experiment is carried out in young (pre-plaque) Aβoverexpressing mice to avoid interference of insoluble Aβ with ELISA determination of soluble Aβ (plaques) in brain. During a stereotaxic surgery under deep anesthesia a guide cannula is implanted into the lateral ventricle. Mice are housed individually after surgery. After at least one week of recovery, an injector is lowered through the guide cannula, which is connected through tubing to an external pump containing artificial CSF. A swivel (rotary joint) is included in the tubing, to allow the mice to move freely around in their cage. In the first set of mice (~5), the maximal tolerable infusion rate is established by slowly increasing the infusion rate while recording clinical signs of distress.

AD mice are bred and the short-term effect of CSF infusion on brain Aβ levels is determined. Besides the CSF-infusion group of AD mice (at max tolerated flow rate) a control group is used to control for the effect of the surgery and presence of a guide cannula on Aβbrain levels. Given considerable variation of Aβlevels between transgenic mice, at least 12 mice are used in each of the groups (n=12 AD mice without infusion, n=12 AD mice with CSF infusion at max flow rate). CSF infusion at maximum speed is continued for 72 hours. Immediately thereafter, animals are sacrificed by perfusion with PBS, followed by dissection of the cortex and hippocampus. ELISA is used to determine Aβ40 and Aβ42 levels in cortex and hippocampus.

To test the effect of CSF infusion in the long-term, AD mice are infused with CSF from the age of 12 weeks (pre-plaque) until the age at which normally the first plaques emerge (24 weeks of age) by surgery and infusion techniques. To control for the effect of long-term CSF infusion, groups of non-AD control mice are provided. Given the variation in cognitive performance among mice, at least 16 mice are used in each of the groups (n=16 AD mice without infusion, n=16 AD mice with CSF infusion, n=16 control mice without infusion, n=16 control mice with CSF infusion). At the age of 24 weeks, mice are tested for cognitive performance in a test of discrimination learning (Cognition-Wall automated home cage task), as well as a test for spatial learning and memory (Morris Water maze). Before each training session in the cognitive tests, mice are released from the CSF infusion pump, and connected to the pump immediately following training. Hereafter, animals are sacrificed by perfusion with PBS, dissection of the cortex and hippocampus. ELISA is used to determine Aβ40 and Aβ42 levels in cortex and hippocampus.

Example 2

Intracranial CSF Infusion in an Animal Model of Glaucoma: The Effect on Optic Nerve and Retinal Ganglion Cell Degeneration A primary open-angle glaucoma rat model is used to study the effect of intracerebroventricular infusion of artificial cerebrospinal fluid on the risk of development or the progression of glaucoma.

A project approval of the Dutch regulatory instances is obtained for all animal experiments described below. During a stereotaxic surgery under deep anesthesia a guide cannula are implanted into the lateral ventricle. The tip of a pressure-monitoring probe (Data Sciences International) is fed through the cannula into the lateral ventricle to allow for measurement of intracranial pressure (ICP). Rats are housed individually after surgery. After at least one week of recovery, an injector is lowered through the guide cannula, which is connected through tubing to an external pump containing artificial CSF. A swivel (rotary joint) is included in the tubing, to allow the rats to move freely around in their cage. In the first set of rats (~5), the maximal tolerable infusion rate is established by slowly increasing the infusion rate while recording clinical signs of distress. While increasing the flow rate, real-time measurements of the ICP are obtained.

After determining the maximum tolerable flow rate, four groups of rats (n=8 per group) are connected for CSF infusion at various flow rates (No, low, intermediate and maximum flow) for a duration of 1 week. To calculate the trans-lamina cribrosa pressure difference (intraocular pressure minus intracranial pressure), intraocular pressure as well as intracranial pressure is measured daily using a rebound tonometer (Tonolab). Hereafter, rats are sacrificed and eyes and optic nerves are dissected out and fixed for staining and analysis of optic nerve and retinal ganglion cell degeneration.

The invention claimed is:

1. A method for the prevention or treatment of glaucoma or retinal dysfunction in a patient in need thereof, said method comprising administering to said patient cerebrospinal fluid (CSF) or artificial CSF in an amount effective to maintain an increase in intracranial pressure (ICP) relative to ICP before starting administration of the CSF or artificial CSF and to prevent or treat glaucoma or retinal dysfunction in a patient,
   wherein administration of the CSF or artificial CSF ensures an ICP between 11 and 16 mmHg in a lateral decubitus position of the patient, and
   wherein the CSF or artificial CSF is administered to the patient using an implantable pump that is controlled by a microcontroller that activates the pump in response to a pressure sensor that monitors the patient's CSF pressure or ICP.

2. The method according to claim 1, wherein CSF or artificial CSF is administered into an intrathecal space or a cerebral ventricle of said patient.

3. The method according to claim 2, wherein said administration reduces a trans-lamina cribrosa pressure difference (TLCPD) in said patient.

4. The method according to claim 2, wherein said administration produces an increase in CSF turnover.

5. The method according to claim 1, wherein the CSF or artificial CSF is administered by an apparatus for infusing fluid into a body cavity, the apparatus comprising:
   the implantable pump;
   a reservoir containing the artificial cerebrospinal fluid;
   an infusion catheter having an inlet end coupled to the reservoir, and an outlet end coupled to the implantable pump; and
   an inflow catheter having an outlet end configured to be disposed in fluid communication with a body cavity, and an inlet end coupled to the implantable pump,
   wherein the implantable pump is configured to selectively move artificial cerebrospinal fluid from the reservoir through the infusion catheter and the inflow catheter to the body cavity at a rate and volume sufficient to replenish, flush, or both, a portion of cerebrospinal fluid in a brain with the artificial cerebrospinal fluid, thereby increasing intracranial pressure in said patient.

6. The method according to claim 5, wherein the pressure sensor is disposed in communication with the inflow catheter to monitor pressure of the cerebrospinal fluid.

7. The method according to claim 5, wherein the microcontroller includes a clock, and further is programmed to activate the pump periodically responsive to the clock to pump a predetermined amount of artificial cerebrospinal fluid from the reservoir to the body cavity.

8. The method according to claim 5, wherein the outlet end of the inflow catheter comprises a flange configured to promote sealing of the brain where the outlet catheter passes therethrough.

9. The method according to claim 5, wherein said apparatus further comprises:
a battery coupled to the implantable pump; and
an implantable inductive charging circuit coupled to the battery.

10. The method according to claim 9, wherein said apparatus further comprises an extracorporeal controller, the extracorporeal controller including an inductive energy transmission circuit configured to transmit energy to the implantable inductive charging circuit.

11. The method of claim 10, wherein the extracorporeal controller receives data from the microcontroller relating to pump activation periods, measured pressures, and actual volumes of artificial cerebrospinal fluid pumped through the inflow catheter.

12. The method of claim 5, wherein the microcontroller is coupled to a first transceiver and the controller is coupled to a second transceiver, and the first and second transceiver communicate information relating to operation of the implantable pump.

13. The method according to claim 5, wherein the microcontroller receives programmed instructions from the controller relating to pump activation intervals and targeted volumes of artificial cerebrospinal fluid to be pumped.

14. The method according to claim 5, wherein said apparatus, further comprises a one-way valve disposed between the reservoir and the outlet end of the inflow catheter, the one-way valve configured to permit artificial cerebrospinal fluid to flow only from the infusion catheter to the inflow catheter.

15. The method according to claim 5, wherein the artificial cerebrospinal fluid comprises one or more therapeutic agents.

16. The method according to claim 5, wherein the reservoir is adapted to be implanted within the patient.

17. The method according to claim 1, wherein the artificial CSF comprises sodium ions at a concentration of 140-190 mM, potassium ions at a concentration of 2.5-4.5 mM, calcium ions at a concentration of 1-1.5 mM, magnesium ions at a concentration of 0.5-1.5 mM, phosphor ions at a concentration of 0.5-1.5 mM, and chloride ions at a concentration of 100-200 mM.

* * * * *